(12) United States Patent
Ellingwood et al.

(10) Patent No.: US 10,441,753 B2
(45) Date of Patent: Oct. 15, 2019

(54) VASCULAR ACCESS CONFIGURATION

(71) Applicant: Arstasis, Inc., Sonoma, CA (US)

(72) Inventors: Brian Andrew Ellingwood, Sunnyvale, CA (US); D. Bruce Modesitt, San Carlos, CA (US)

(73) Assignee: Arstasis, Inc., Sonoma, CA (US)

( * ) Notice: Subject to any disclaimer, the term of this patent is extended or adjusted under 35 U.S.C. 154(b) by 0 days.

(21) Appl. No.: 15/627,203

(22) Filed: Jun. 19, 2017

(65) Prior Publication Data

US 2017/0281908 A1 Oct. 5, 2017

Related U.S. Application Data

(63) Continuation of application No. 15/238,668, filed on Aug. 16, 2016, now abandoned, which is a continuation of application No. 14/940,109, filed on Nov. 12, 2015, now abandoned, which is a (Continued)

(51) Int. Cl.
| | |
|---|---|
| *A61M 29/00* | (2006.01) |
| *A61M 25/06* | (2006.01) |
| *A61B 17/34* | (2006.01) |
| *A61M 25/09* | (2006.01) |

(Continued)

(52) U.S. Cl.
CPC ..... *A61M 25/0662* (2013.01); *A61B 17/3415* (2013.01); *A61M 25/09* (2013.01); *A61M 29/00* (2013.01); *A61M 39/0247* (2013.01); *A61M 25/02* (2013.01); *A61M 2025/0293* (2013.01);

(Continued)

(58) Field of Classification Search
CPC .................. A61M 29/00; A61M 29/02; A61M 2025/0687; A61M 25/0069
See application file for complete search history.

(56) References Cited

U.S. PATENT DOCUMENTS

| | | |
|---|---|---|
| 672,377 A | 4/1901 | Kearns |
| 2,751,911 A | 1/1953 | Held |
| 2,857,925 A | 6/1955 | Higginbotham |

(Continued)

FOREIGN PATENT DOCUMENTS

| | | |
|---|---|---|
| CN | 1823687 A | 8/2006 |
| CN | 101431948 A | 5/2009 |

(Continued)

OTHER PUBLICATIONS

Extended European Search Report dated Apr. 4, 2016, European Patent Application 13825135.0, (10 pages).

(Continued)

*Primary Examiner* — William R Carpenter
(74) *Attorney, Agent, or Firm* — Stephen M. De Klerk

(57) ABSTRACT

One embodiment is directed to a system for creating translumenal vascular access, comprising a dilator adaptor member having proximal and distal ends and defining a dilator adaptor lumen therethrough, wherein the dilator adaptor lumen is defined by an inner diameter profile sized to accommodate insertion of one or more portions of a guidewire, and wherein the dilator adaptor is further defined by an outer diameter profile sized to accommodate at least partial insertion of the proximal end of the dilator adaptor into a dilator member lumen formed through a dilator member, the dilator member being coupleable to an introducer catheter member through an introducer member lumen formed through the introducer member.

17 Claims, 15 Drawing Sheets

Related U.S. Application Data continuation of application No. 13/902,579, filed on May 24, 2013, now abandoned.

(60) Provisional application No. 61/652,104, filed on May 25, 2012.

(51) Int. Cl.
*A61M 39/02* (2006.01)
*A61M 25/02* (2006.01)

(52) U.S. Cl.
CPC .............. *A61M 2039/0258* (2013.01); *A61M 2039/0273* (2013.01)

(56) References Cited

U.S. PATENT DOCUMENTS

| | | |
|---|---|---|
| 3,598,118 A | 8/1971 | Warren |
| 3,727,614 A | 4/1973 | Kniazuk |
| 3,730,185 A | 5/1973 | Cook et al. |
| 3,908,637 A | 9/1975 | Doroshow |
| 4,006,747 A | 2/1977 | Kronenthal et al. |
| 4,629,450 A | 12/1986 | Suzuki et al. |
| 4,744,364 A | 5/1988 | Kensey |
| 4,765,332 A | 8/1988 | Fishcell et al. |
| 4,850,960 A | 7/1989 | Grayzel |
| 4,890,611 A | 1/1990 | Monfort et al. |
| 4,921,484 A | 5/1990 | Hillstead |
| 4,955,897 A | 9/1990 | Ship |
| 4,962,755 A | 10/1990 | King et al. |
| 5,074,846 A | 12/1991 | Clegg et al. |
| 5,133,364 A | 7/1992 | Palermo et al. |
| 5,183,464 A | 2/1993 | Dubrul et al. |
| 5,188,620 A | 2/1993 | Jepson et al. |
| 5,271,415 A | 12/1993 | Foerster et al. |
| 5,304,184 A | 4/1994 | Hathaway et al. |
| 5,320,639 A | 6/1994 | Rudnick |
| 5,336,221 A | 8/1994 | Anderson |
| 5,336,252 A | 8/1994 | Cohen |
| 5,358,507 A | 10/1994 | Daily |
| 5,364,359 A | 11/1994 | van den Haak |
| 5,364,389 A | 11/1994 | Anderson |
| 5,368,601 A | 11/1994 | Sauer et al. |
| 5,380,290 A | 1/1995 | Makower et al. |
| 5,383,897 A | 1/1995 | Wholey |
| 5,391,182 A | 2/1995 | Chin |
| 5,391,183 A | 2/1995 | Janzen et al. |
| 5,403,329 A | 4/1995 | Hinchcliffe |
| 5,415,657 A | 5/1995 | Taymor-Luria |
| 5,417,699 A | 5/1995 | Klein et al. |
| 5,437,665 A | 8/1995 | Munro |
| 5,439,469 A | 8/1995 | Heaven et al. |
| 5,451,230 A | 9/1995 | Steinert |
| 5,462,561 A | 10/1995 | Voda |
| 5,467,786 A | 11/1995 | Allen et al. |
| 5,470,338 A | 11/1995 | Whitfield et al. |
| 5,474,568 A | 12/1995 | Scott |
| 5,476,470 A | 12/1995 | Fitzgibbons, Jr. |
| 5,489,288 A | 2/1996 | Buelna |
| 5,496,332 A | 3/1996 | Sierra et al. |
| 5,496,334 A | 3/1996 | Klundt et al. |
| 5,503,634 A | 4/1996 | Christy |
| 5,507,731 A | 4/1996 | Hernandez et al. |
| 5,507,744 A | 4/1996 | Tay et al. |
| 5,527,321 A | 6/1996 | Hinchliffe |
| 5,527,322 A | 6/1996 | Klein et al. |
| 5,536,255 A | 7/1996 | Moss |
| 5,571,169 A | 11/1996 | Plaia et al. |
| 5,613,974 A | 3/1997 | Andreas et al. |
| 5,620,461 A | 4/1997 | Muijs Van De Moer et al. |
| 5,622,188 A | 4/1997 | Plaia et al. |
| 5,645,566 A | 7/1997 | Brenneman et al. |
| 5,653,717 A | 8/1997 | Ko et al. |
| 5,695,504 A | 12/1997 | Gifford, III et al. |
| 5,700,273 A | 12/1997 | Buelna et al. |
| 5,702,438 A | 12/1997 | Avitall |
| 5,709,224 A | 1/1998 | Behl et al. |
| 5,746,755 A | 5/1998 | Wood et al. |
| 5,749,858 A | 5/1998 | Cramer |
| 5,758,665 A | 6/1998 | Suval |
| 5,762,066 A | 6/1998 | Law et al. |
| 5,766,183 A | 6/1998 | Sauer |
| 5,772,673 A | 6/1998 | Cuny et al. |
| 5,779,719 A | 7/1998 | Klein et al. |
| 5,792,152 A | 8/1998 | Klein et al. |
| 5,797,929 A | 8/1998 | Andreas et al. |
| 5,810,810 A | 9/1998 | Tay et al. |
| 5,810,822 A | 9/1998 | Bolduc et al. |
| 5,810,849 A | 9/1998 | Kontos |
| 5,817,108 A | 10/1998 | Poncet |
| 5,830,232 A | 11/1998 | Hasson |
| 5,836,955 A | 11/1998 | Buelna et al. |
| 5,846,253 A | 12/1998 | Buelna et al. |
| 5,860,990 A | 1/1999 | Nobles et al. |
| 5,860,991 A | 1/1999 | Klein et al. |
| 5,868,762 A | 2/1999 | Cragg et al. |
| 5,876,411 A | 3/1999 | Kontos |
| 5,882,302 A | 3/1999 | Driscoll, Jr. et al. |
| 5,902,311 A | 5/1999 | Andreas et al. |
| 5,921,994 A | 7/1999 | Andreas et al. |
| 5,928,246 A | 7/1999 | Gordon et al. |
| 5,941,897 A | 8/1999 | Myers |
| 5,954,732 A | 9/1999 | Hart et al. |
| 5,972,005 A | 10/1999 | Stalker et al. |
| 5,972,013 A | 10/1999 | Schmidt |
| 5,980,539 A | 11/1999 | Kontos |
| 5,984,917 A | 11/1999 | Fleischman et al. |
| 5,984,948 A | 11/1999 | Hasson |
| 5,984,950 A | 11/1999 | Cragg et al. |
| 6,010,514 A | 1/2000 | Burney et al. |
| 6,033,401 A | 3/2000 | Edwards et al. |
| 6,036,699 A | 3/2000 | Andreas et al. |
| 6,036,721 A | 3/2000 | Harren et al. |
| 6,042,601 A | 3/2000 | Smith |
| 6,063,085 A | 5/2000 | Tay et al. |
| 6,071,292 A | 6/2000 | Makower et al. |
| 6,071,300 A | 6/2000 | Brenneman et al. |
| 6,077,276 A | 6/2000 | Kontos |
| 6,080,175 A | 6/2000 | Hogendijk |
| 6,093,173 A | 7/2000 | Balceta et al. |
| 6,117,144 A | 9/2000 | Nobles et al. |
| 6,117,145 A | 9/2000 | Wood et al. |
| 6,136,010 A | 10/2000 | Modesitt et al. |
| 6,139,560 A | 10/2000 | Kremer |
| 6,143,004 A | 11/2000 | Davis et al. |
| 6,146,397 A | 11/2000 | Harkrider, Jr. |
| 6,152,918 A | 11/2000 | Padilla et al. |
| 6,159,232 A | 12/2000 | Nowakowski |
| 6,171,317 B1 | 1/2001 | Jackson et al. |
| 6,179,832 B1 | 1/2001 | Jones et al. |
| 6,190,396 B1 | 2/2001 | Whitin et al. |
| 6,197,042 B1 | 3/2001 | Ginn et al. |
| 6,203,554 B1 | 3/2001 | Roberts |
| 6,206,893 B1 | 3/2001 | Klein et al. |
| 6,206,895 B1 | 3/2001 | Levinson |
| 6,245,079 B1 | 6/2001 | Nobles et al. |
| 6,258,084 B1 | 7/2001 | Goldman et al. |
| 6,302,898 B1 | 10/2001 | Edwards et al. |
| 6,358,244 B1 | 3/2002 | Newman et al. |
| 6,358,556 B1 | 3/2002 | Ding et al. |
| 6,371,975 B2 | 4/2002 | Cruise et al. |
| 6,383,208 B1 | 5/2002 | Sancoff et al. |
| 6,395,015 B1 | 5/2002 | Borst et al. |
| 6,398,782 B1 | 6/2002 | Pecor et al. |
| 6,454,777 B1 | 9/2002 | Green |
| 6,457,182 B1 | 10/2002 | Szczesuil et al. |
| 6,458,147 B1 | 10/2002 | Cruise et al. |
| 6,461,383 B1 | 10/2002 | Gesswein et al. |
| 6,468,228 B1 | 10/2002 | Topel et al. |
| 6,475,182 B1 | 11/2002 | Hnojewyj et al. |
| 6,506,210 B1 | 1/2003 | Kanner |
| 6,517,553 B2 | 2/2003 | Klein et al. |
| 6,524,321 B2 | 2/2003 | Kanesaka |
| 6,524,326 B1 | 2/2003 | Zhu et al. |

(56) References Cited

U.S. PATENT DOCUMENTS

| | | |
|---|---|---|
| 6,533,795 B1 | 3/2003 | Tran et al. |
| 6,562,059 B2 | 5/2003 | Edwards et al. |
| 6,565,583 B1 | 5/2003 | Deaton et al. |
| 6,569,012 B2 | 5/2003 | Lydon et al. |
| 6,622,731 B2 | 9/2003 | Daniel et al. |
| 6,623,510 B2 | 9/2003 | Carley et al. |
| 6,626,855 B1 | 9/2003 | Weng et al. |
| 6,641,592 B1 | 11/2003 | Sauer et al. |
| 6,656,136 B1 | 12/2003 | Weng et al. |
| 6,663,655 B2 | 12/2003 | Ginn et al. |
| 6,676,685 B2 | 1/2004 | Pedros et al. |
| 6,682,489 B2 | 1/2004 | Tenerz et al. |
| 6,689,152 B2 | 2/2004 | Balceta et al. |
| 6,719,694 B2 | 4/2004 | Weng et al. |
| 6,719,750 B2 | 4/2004 | Varner et al. |
| 6,733,515 B1 | 5/2004 | Edwards et al. |
| 6,743,195 B2 | 6/2004 | Zucker |
| 6,749,621 B2 | 6/2004 | Pantages et al. |
| 6,749,622 B2 | 6/2004 | McGuckin, Jr. et al. |
| 6,767,356 B2 | 7/2004 | Kanner et al. |
| 6,773,699 B1 | 8/2004 | Soltz et al. |
| 6,780,197 B2 | 8/2004 | Roe et al. |
| 6,790,220 B2 | 9/2004 | Morris et al. |
| 6,802,822 B1 | 10/2004 | Dodge |
| 6,818,008 B1 | 11/2004 | Cates et al. |
| 6,840,952 B2 | 1/2005 | Saker et al. |
| 6,843,792 B2 | 1/2005 | Nishtala et al. |
| 6,846,319 B2 | 1/2005 | Ginn et al. |
| 6,846,320 B2 | 1/2005 | Ashby et al. |
| 6,846,321 B2 | 1/2005 | Zucker |
| 6,860,895 B1 | 3/2005 | Akerfeldt et al. |
| 6,863,680 B2 | 3/2005 | Ashby |
| 6,890,342 B2 | 5/2005 | Zhu et al. |
| 6,890,343 B2 | 5/2005 | Ginn et al. |
| 6,890,344 B2 | 5/2005 | Levinson |
| 6,893,431 B2 | 5/2005 | Naimark et al. |
| 6,896,692 B2 | 5/2005 | Ginn et al. |
| 6,918,890 B2 | 7/2005 | Schmidt |
| 6,929,655 B2 | 8/2005 | Egnelov et al. |
| 6,936,053 B1 | 8/2005 | Weiss |
| 6,939,348 B2 | 9/2005 | Malecki et al. |
| 6,939,357 B2 | 9/2005 | Navarro et al. |
| 6,939,363 B2 | 9/2005 | Akerfeldt |
| 6,939,364 B1 | 9/2005 | Soltz et al. |
| 6,942,674 B2 | 9/2005 | Belef et al. |
| 6,949,080 B2 | 9/2005 | Wolf et al. |
| 6,949,107 B2 | 9/2005 | McGuckin, Jr. et al. |
| 6,949,114 B2 | 9/2005 | Milo et al. |
| 6,964,668 B2 | 11/2005 | Modesitt et al. |
| 6,964,675 B2 | 11/2005 | Zhu et al. .......... 606/213 |
| 6,969,397 B2 | 11/2005 | Ginn |
| 6,981,983 B1 | 1/2006 | Rosenblatt et al. |
| 6,994,686 B2 | 2/2006 | Cruise et al. |
| 6,997,900 B2 | 2/2006 | Weststrate et al. ......... 604/104 |
| 7,001,400 B1 | 2/2006 | Modesitt et al. |
| 7,008,440 B2 | 3/2006 | Sing et al. |
| 7,008,442 B2 | 3/2006 | Brightbill |
| 7,025,746 B2 | 4/2006 | Tal |
| 7,025,776 B1 | 4/2006 | Houser et al. |
| 7,029,489 B1 | 4/2006 | Ashby et al. |
| 7,037,322 B1 | 5/2006 | Sing et al. |
| 7,037,323 B2 | 5/2006 | Sing et al. |
| 7,041,119 B2 | 5/2006 | Green |
| 7,074,232 B2 | 7/2006 | Kanner et al. |
| 7,077,848 B1 | 7/2006 | de Juan, Jr. et al. |
| 7,081,125 B2 | 7/2006 | Edwards et al. |
| 7,083,628 B2 | 8/2006 | Bachmen |
| 7,141,055 B2 | 11/2006 | Abrams et al. |
| 7,175,646 B2 | 2/2007 | Brenneman |
| 7,179,270 B2 | 2/2007 | Makower |
| 7,182,763 B2 | 2/2007 | Nardella |
| 7,186,251 B2 | 3/2007 | Malecki et al. |
| 7,226,467 B2 | 6/2007 | Lucatero et al. |
| 7,235,087 B2 | 6/2007 | Modesitt et al. |
| 7,247,162 B1 | 7/2007 | Thornton |
| 7,250,028 B2 | 7/2007 | Julian et al. |
| 7,279,001 B2 | 10/2007 | Addis et al. |
| 7,291,159 B2 | 11/2007 | Schmelzeisen-Redeker et al. |
| 7,293,562 B2 | 11/2007 | Malecki et al. |
| 7,316,704 B2 | 1/2008 | Bagaoisan et al. |
| 7,322,976 B2 | 1/2008 | Yassinzadeh |
| 7,335,220 B2 | 2/2008 | Khosravi et al. |
| 7,351,214 B2 | 4/2008 | Burgermeister |
| 7,361,180 B2 | 4/2008 | Saadat et al. |
| 7,361,183 B2 | 4/2008 | Ginn |
| 7,377,927 B2 | 5/2008 | Burdulis et al. |
| 7,381,210 B2 | 6/2008 | Zarbatany et al. |
| 7,390,328 B2 | 6/2008 | Modesitt |
| 7,390,329 B2 | 6/2008 | Westra et al. |
| 7,470,237 B2 | 12/2008 | Beckman et al. |
| 7,494,460 B2 | 2/2009 | Haarstad et al. |
| 7,572,274 B2 | 8/2009 | Yassinzadeh |
| 7,597,705 B2 | 10/2009 | Forsberg et al. |
| 7,609,673 B2 | 10/2009 | Bergenlid et al. |
| 7,621,925 B2 | 11/2009 | Saadat et al. |
| 7,621,936 B2 | 11/2009 | Cragg et al. |
| 7,635,329 B2 | 12/2009 | Goldfarb et al. |
| 7,648,517 B2 | 1/2010 | Makower et al. |
| 7,662,128 B2 | 2/2010 | Salcudean et al. |
| 7,678,133 B2 | 3/2010 | Modesitt |
| 7,704,261 B2 | 4/2010 | Sakamoto et al. |
| 7,704,264 B2 | 4/2010 | Ewers et al. |
| 7,731,726 B2 | 6/2010 | Belhe et al. |
| 7,736,347 B2 | 6/2010 | Kaplan et al. |
| 7,747,314 B2 | 6/2010 | Parins et al. |
| 7,762,977 B2 | 7/2010 | Porter et al. |
| 7,837,696 B2 | 11/2010 | Modesitt et al. |
| 7,842,047 B2 | 11/2010 | Modesitt et al. |
| 7,846,170 B2 | 12/2010 | Modesitt et al. |
| 7,850,654 B2 | 12/2010 | Belhe et al. |
| 7,850,701 B2 | 12/2010 | Modesitt et al. |
| 7,867,249 B2 | 1/2011 | Palermo et al. |
| 7,875,052 B2 | 1/2011 | Kawaura et al. |
| 7,967,839 B2 | 6/2011 | Flock et al. |
| 8,021,362 B2 | 9/2011 | Deem et al. |
| 8,187,231 B2 | 5/2012 | Bellisario et al. ....... 604/164.06 |
| 2001/0031922 A1 | 10/2001 | Weng et al. |
| 2001/0047165 A1 | 11/2001 | Makower et al. |
| 2002/0016614 A1 | 2/2002 | Klein et al. |
| 2002/0062146 A1 | 5/2002 | Makower et al. |
| 2002/0156495 A1 | 10/2002 | Brenneman et al. |
| 2003/0093093 A1 | 5/2003 | Modesitt et al. |
| 2003/0100921 A1 | 5/2003 | Addis et al. |
| 2003/0144679 A1 | 7/2003 | Irisawa |
| 2003/0158578 A1 | 8/2003 | Pantages et al. |
| 2003/0187333 A1 | 10/2003 | Spence |
| 2003/0233120 A1 | 12/2003 | Akerfeldt |
| 2003/0236542 A1 | 12/2003 | Makower |
| 2004/0044350 A1 | 3/2004 | Martin et al. |
| 2004/0068242 A1 | 4/2004 | McGuckin, Jr. |
| 2004/0086951 A1 | 5/2004 | Archakov et al. |
| 2004/0092875 A1 | 5/2004 | Kochamba |
| 2004/0092964 A1 | 5/2004 | Modesitt et al. |
| 2004/0093024 A1 | 5/2004 | Lousararian et al. |
| 2004/0097978 A1 | 5/2004 | Modesitt et al. |
| 2004/0122449 A1 | 6/2004 | Modesitt et al. |
| 2004/0138522 A1 | 7/2004 | Haarstad et al. |
| 2004/0143290 A1 | 7/2004 | Brightbill |
| 2004/0153123 A1 | 8/2004 | Palermo et al. |
| 2004/0158287 A1 | 8/2004 | Cragg et al. |
| 2004/0172058 A1 | 9/2004 | Edwards et al. |
| 2004/0176758 A1 | 9/2004 | Yassinzadeh et al. |
| 2004/0215232 A1 | 10/2004 | Belhe et al. |
| 2004/0215233 A1 | 10/2004 | Kaplan et al. |
| 2004/0220594 A1 | 11/2004 | de Canniere |
| 2004/0220604 A1 | 11/2004 | Fogarty et al. |
| 2004/0267307 A1 | 12/2004 | Bagaoisan et al. |
| 2004/0267308 A1 | 12/2004 | Bagaoisan et al. |
| 2005/0033361 A1 | 2/2005 | Galdonik et al. |
| 2005/0049634 A1 | 3/2005 | Chopra |
| 2005/0075653 A1 | 4/2005 | Saadat et al. |
| 2005/0085773 A1 | 4/2005 | Forsberg |
| 2005/0085851 A1 | 4/2005 | Fiehler et al. |
| 2005/0085852 A1 | 4/2005 | Ditter |

(56) References Cited

U.S. PATENT DOCUMENTS

| | | |
|---|---|---|
| 2005/0085854 A1 | 4/2005 | Ginn |
| 2005/0085855 A1 | 4/2005 | Forsberg |
| 2005/0085856 A1 | 4/2005 | Ginn |
| 2005/0090860 A1 | 4/2005 | Paprocki |
| 2005/0096697 A1 | 5/2005 | Forsberg et al. |
| 2005/0107826 A1 | 5/2005 | Zhu et al. |
| 2005/0125030 A1 | 6/2005 | Forsberg et al. |
| 2005/0143761 A1 | 6/2005 | Modesitt et al. |
| 2005/0149049 A1 | 7/2005 | Assell et al. |
| 2005/0149065 A1 | 7/2005 | Modesitt |
| 2005/0209564 A1 | 9/2005 | Bonner et al. |
| 2005/0228443 A1 | 10/2005 | Yassinzadeh |
| 2005/0234507 A1 | 10/2005 | Geske et al. |
| 2005/0245945 A1 | 11/2005 | Ewers et al. |
| 2005/0251189 A1 | 11/2005 | Saadat et al. |
| 2005/0267520 A1 | 12/2005 | Modesitt |
| 2005/0267522 A1 | 12/2005 | Yassinzadeh et al. |
| 2005/0277967 A1 | 12/2005 | Brenneman et al. |
| 2005/0277980 A1 | 12/2005 | Yassinzadeh |
| 2006/0009794 A1 | 1/2006 | Ninomiya et al. |
| 2006/0009802 A1 | 1/2006 | Modesitt |
| 2006/0036218 A1 | 2/2006 | Goodson, IV et al. |
| 2006/0064101 A1 | 3/2006 | Aaramon |
| 2006/0064159 A1 | 3/2006 | Porter et al. |
| 2006/0069396 A1 | 3/2006 | Meade et al. |
| 2006/0079914 A1 | 4/2006 | Modesitt et al. |
| 2006/0111741 A1 | 5/2006 | Nardella |
| 2006/0129100 A1 | 6/2006 | Tal ............................ 604/164.1 |
| 2006/0129101 A1 | 6/2006 | McGuckin, Jr. |
| 2006/0135990 A1 | 6/2006 | Johnson |
| 2006/0135991 A1 | 6/2006 | Kawaura et al. |
| 2006/0136035 A1 | 6/2006 | Hermann et al. |
| 2006/0142785 A1 | 6/2006 | Modesitt et al. |
| 2006/0167476 A1 | 7/2006 | Burdulis, Jr. et al. |
| 2006/0206125 A1 | 9/2006 | Fogarty et al. |
| 2006/0217664 A1 | 9/2006 | Hattler et al. |
| 2006/0235449 A1 | 10/2006 | Schubart et al. |
| 2006/0259017 A1 | 11/2006 | Heil, Jr. |
| 2006/0264975 A1 | 11/2006 | Pipenhagen et al. |
| 2006/0271078 A1 | 11/2006 | Modesitt |
| 2007/0027454 A1 | 2/2007 | Modesitt |
| 2007/0027455 A1 | 2/2007 | Modesitt |
| 2007/0032802 A1 | 2/2007 | Modesitt |
| 2007/0032803 A1 | 2/2007 | Modesitt |
| 2007/0032804 A1 | 2/2007 | Modesitt |
| 2007/0106246 A1 | 5/2007 | Modesitt |
| 2007/0167959 A1 | 7/2007 | Modesitt et al. |
| 2007/0255208 A1 | 11/2007 | McMichael et al. |
| 2007/0255313 A1 | 11/2007 | Modesitt |
| 2008/0051821 A1 | 2/2008 | Gephart ........................ 606/191 |
| 2008/0097347 A1 | 4/2008 | Arvanaghi |
| 2008/0114364 A1 | 5/2008 | Goldin et al. |
| 2008/0215733 A1 | 9/2008 | Yodfat et al. |
| 2008/0269687 A1 | 10/2008 | Chong et al. |
| 2009/0005793 A1 | 1/2009 | Pantages et al. |
| 2009/0105744 A1 | 4/2009 | Modesitt et al. |
| 2009/0125097 A1 | 5/2009 | Bruszewski et al. |
| 2009/0292312 A1 | 11/2009 | Tochimura et al. |
| 2009/0306472 A1 | 12/2009 | Filipi et al. |
| 2009/0312786 A1 | 12/2009 | Trask et al. |
| 2009/0318889 A1 | 12/2009 | Modesitt |
| 2010/0016786 A1 | 1/2010 | Drews et al. |
| 2010/0016810 A1 | 1/2010 | Drews et al. |
| 2010/0063375 A1 | 3/2010 | Kassab et al. |
| 2010/0125296 A1 | 5/2010 | Modesitt |
| 2010/0174281 A1 | 7/2010 | Jahns et al. |
| 2010/0179588 A1 | 7/2010 | Sater et al. |
| 2010/0198328 A1 | 8/2010 | Hartley et al. |
| 2011/0011525 A1 | 1/2011 | Sanscoucy |
| 2011/0125178 A1 | 5/2011 | Drews et al. |
| 2011/0208215 A1 | 8/2011 | Modesitt et al. |
| 2011/0230906 A1 | 9/2011 | Modesitt et al. |

FOREIGN PATENT DOCUMENTS

| | | |
|---|---|---|
| EP | 0637431 | 2/1995 |
| EP | 0910288 B1 | 8/2002 |
| EP | 145691 | 9/2004 |
| EP | 1459692 A1 | 9/2004 |
| EP | 1518507 A1 | 3/2005 |
| EP | 2452719 A1 | 5/2012 |
| JP | 2-71764 | 3/1990 |
| JP | 2000-175930 | 6/2000 |
| JP | 2002-531229 | 9/2002 |
| JP | 2002-330973 | 11/2002 |
| JP | 2003-126024 | 5/2003 |
| JP | 2008-541877 A | 11/2008 |
| WO | 00/33909 | 6/2000 |
| WO | WO-2001/012012 | 2/2001 |
| WO | WO-2001/066018 | 9/2001 |
| WO | WO 2003/082363 | 10/2003 |
| WO | WO-2005/112791 | 12/2005 |
| WO | 2006/017023 A2 | 2/2006 |
| WO | WO-2006/017023 | 2/2006 |
| WO | WO 2006/017023 A1 | 2/2006 |
| WO | 2006/124896 A2 | 11/2006 |
| WO | WO-2006/124896 | 11/2006 |
| WO | 2008/042034 A2 | 4/2008 |
| WO | WO 2008/042034 | 4/2008 |
| WO | WO 2008/070238 | 6/2008 |
| WO | 2008/089424 A | 7/2008 |
| WO | 2008/097955 A1 | 8/2008 |
| WO | WO 2008/097955 | 8/2008 |

OTHER PUBLICATIONS

Office Action dated Mar. 14, 2017 with English Translation, Japanese Patent Application No. 2015-514235, (13 pages).

Patent Examination Report No. 1 dated Oct. 27, 2016, Australian Patent Application No. 2013266115, (4 pages).

Communication Pursuant to Article 94(3) EPC dated Feb. 12, 2018, European Patent Application No. 13793912.3, (6 pages).

Non Final Office Action dated Oct. 20, 2017, U.S. Appl. No. 14/973,670, (60 pages).

Final Office Action dated Aug. 11, 2016, U.S. Appl. No. 13/902,599, (15 pages).

Final Office Action dated Mar. 20, 2017, U.S. Appl. No. 13/902,599, (16 pages).

Final Office Action dated Nov. 27, 2015, U.S. Appl. No. 13/902,599, (12 pages).

Office Action dated Mar. 31, 2015, U.S. Appl. No. 13/902,599, (10 pages).

International Search Report, dated Aug. 20, 2007, for PCT Application No. PCT/US06/18915 filed on May 12, 2006, 2 pages.

Franklin, I.J. et al. (1999). "Uptake of Tetracycline by Aortic Aneurysm Wall and Its Effect on Inflammation and Proteolysis," Brit. J. Surgery 86(6):771-775.

Pyo, R. et al. (Jun. 2000). "Targeted Gene Disruption of Matrix Metalloproteinase-9 (Gelatinase B) Suppresses Development of Experimental Abdominal Aortic Aneurysms," J. Clinical Investigation 105(11):1641-1649.

Tambiah, J. et al. (2001). "Provocation of Experimental Aortic Inflammation and Dilatation by Inflammatory Mediators and Chlamydia pneumoniae," Brit. J. Surgery 88(7):935-940.

Walton, L.J. et al. (Jul. 6, 1999). "Inhibition of Prostaglandin E.sub.2 Synthesis in Abdominal Aortic Aneurysms," Circulation 100:48-54.

Xu, Q. et al. (Aug. 11, 2000). "Sp1 Increases Expression of Cyclooxygenase-2 in Hypoxic Vascular Endothelium," J. Biological Chemistry 275(32):24583-24589.

Non-Final Office Action dated Oct. 29, 2008, for U.S. Appl. No. 11/788,509, filed Apr. 19, 2007, eight pages.

Non-Final Office Action dated Nov. 12, 2008, for U.S. Appl. No. 10/844,247, filed May 12, 2004, nine pages.

Non-Final Office Action dated Jul. 31, 2008, for U.S. Appl. No. 10/888,682, filed Jul. 10, 2004, 12 pages.

(56) References Cited

OTHER PUBLICATIONS

International Search Report dated Jun. 5, 2008, for PCT Application No. PCT/US05/23107 filed Jun. 30, 2005, two pages.
International Search Report dated Aug. 8, 2008, for PCT Application No. PCT/US05/16623 filed May 12, 2005, three pages.
Non-Final Office Action mailed Oct. 8, 2008, for U.S. Appl. No. 11/432,982, filed May 12, 2006, seven pages.
Non-Final Office Action mailed Jan. 9, 2009, for U.S. Appl. No. 11/544,317, filed Oct. 6, 2006, 11 pages.
International Preliminary Report on Patentability dated Mar. 5, 2009, for PCT Application No. PCT/US2005/016623, filed on May 12, 2005, five pages.
Final Office Action dated Jun. 11, 2009, for U.S. Appl. No. 11/432,982, filed May 12, 2006, seven pages.
Final Office Action mailed on May 6, 2009, for U.S. Appl. No. 10/888,682, filed Jul. 10, 2004, eight pages.
International Preliminary Report on Patentability dated Mar. 3, 2009, for PCT Application No. PCT/US2005/023107, filed on Jun. 30, 2005, five pages.
International Preliminary Report on Patentability dated Nov. 14, 2007, for PCT Application No. PCT/US2006/018915, filed on May 12, 2006, five pages.
Non-Final Office Action dated Feb. 18, 2009, for U.S. Appl. No. 11/545,272, filed Oct. 6, 2006, seven pages.
Non-Final Office Action dated Feb. 23, 2009, for U.S. Appl. No. 11/544,196, filed Oct. 6, 2006, seven pages.
Non-Final Office Action dated Feb. 23, 2009, for U.S. Appl. No. 11/544,365, filed Oct. 6, 2006, six pages.
Non-Final Office Action dated Feb. 24, 2009, for U.S. Appl. No. 11/544,177, filed Oct. 6, 2006, seven pages.
European Search Report dated Jun. 26, 2009, for EP Patent Application No. 08011884.7, filed on May 12, 2005, five pages.
Final Office Action dated Jul. 6, 2009, for U.S. Appl. No. 10/844,247, filed May 12, 2004, nine pages.
Final Office Action dated Aug. 21, 2009, for U.S. Appl. No. 11/788,509, filed Apr. 19, 2007, ten pages.
Final Office Action dated Aug. 14, 2009, for U.S. Appl. No. 11/544,317, filed Oct. 6, 2006, eight pages.
International Search Report dated Sep. 3, 2009, for PCT Application No. PCT/US2009/051317, filed on Jul. 21, 2009, three pages.
Invitation to Pay Additional Fees dated Sep. 10, 2009, for PCT Application No. PCT/US09/51320, filed on Jul. 21, 2009, two pages.
Written Opinion dated Aug. 20, 2007, for PCT Application No. PCT/US06/18915, filed on May 12, 2006, four pages.
Written Opinion dated Jun. 5, 2008, for PCT Application No. PCT/US05/23107, filed on Jun. 30, 2005, four pages.
Written Opinion dated Aug. 8, 2008, for PCT Application No. PCT/US05/16623, filed on May 12, 2005, three pages.
Written Opinion dated Sep. 3, 2009, for PCT Application No. PCT/US2009/051317, filed on Jul. 21, 2009, seven pages.
Final Office Action dated Nov. 18, 2009, for U.S. Appl. No. 11/544,365, filed Oct. 6, 2006, 6 pages.
Final Office Action dated Nov. 25, 2009, for U.S. Appl. No. 11/544,177, filed Oct. 6, 2006, 8 pages.
Final Office Action dated Nov. 25, 2009, for U.S. Appl. No. 11/545,272, filed Oct. 6, 2006, 6 pages.
Final Office Action dated Nov. 27, 2009, for U.S. Appl. No. 11/544,196, filed Oct. 6, 2006, 6 pages.
Non-Final Office Action dated Apr. 15, 2010, for U.S. Appl. No. 11/432,982, filed May 12, 2006, eight pages.
Notice of Allowance dated Nov. 3, 2009, for U.S. Appl. No. 10/888,682, filed Jul. 10, 2004, 9 pages.
Non-final office action dated Mar. 28, 2011, for related U.S. Appl. No. 12/467,251, Inventor D. Bruce Modesitt, filed May 15, 2009, (11 pages).
Office action for related AU Patent Application No. 2006247355, dated Mar. 16, 2011, (16 pages).
File history for related U.S. Appl. No. 10/844,247, filed May 12, 2004, Inventor D. Bruce Modesitt, including (211 pages total): Amendment Response to Final Office Action dated Jul. 6, 2009, for U.S. Appl. No. 10/844,247, submitted on Dec. 7, 2009; Examiner Interview Summary Record for U.S. Appl. No. 10/844,247, dated Sep. 30, 2009; Final Office Action for U.S. Appl. No. 10/844,247, dated Jul. 6, 2009; Applicants Arguments/Remarks Made in an Amendment in Response to Examiner Interview Summary Record dated Mar. 24, 2009, for U.S. Appl. No. 10/844,247, submitted on Apr. 9, 2009; Examiner Interview Summary Record for U.S. Appl. No. 10/844,247, dated Mar. 24, 2009; Amendment Response to Non Final Office Action dated Nov. 12, 2008, for U.S. Appl. No. 10/844,247, submitted on Mar. 12, 2009; Non Final Office Action for U.S. Appl. No. 10/844,247, dated Nov. 12, 2008; Response to Election/Restriction dated Jun. 16, 2008 for U.S. Appl. No. 10/844,247, submitted on Jul. 16, 2008; Requirement for Restriction/Election for U.S. Appl. No. 10/844,247, dated Jun. 16, 2008; Examiner Interview Summary Record for U.S. Appl. No. 10/844,247, dated Oct. 9, 2007; Amendment Response to Final Office Action dated Jun. 28, 2007, for U.S. Appl. No. 10/844,247, submitted on Sep. 27, 2007; Final Office Action for U.S. Appl. No. 10/844,247, dated Jun. 28, 2007; Amendment Response to Non Final Office Action dated Jan. 4, 2007, for U.S. Appl. No. 10/844,247, submitted on Apr. 4, 2007; Non Final Office Action for U.S. Appl. No. 10/844,247, dated Jan. 4, 2007; Response to Election/Restriction dated Sep. 28, 2006 for U.S. Appl. No. 10/844,247, submitted on Oct. 31, 2006; Requirement for Restriction/Election for U.S. Appl. No. 10/844,247, dated Sep. 28, 2006; Application for U.S. Appl. No. 10/844,247, filed May 12, 2004.
File history for related U.S. Appl. No. 11/544,196, filed Oct. 6, 2006, Inventor D. Bruce Modesitt, including (126 pages total): Terminal Disclaimer for U.S. Appl. No. 11/544,196, submitted Mar. 18, 2011; Amendment Response to Non Final Office Action dated Jun. 23, 2010, for U.S. Appl. No. 11/544,196, submitted on Dec. 23, 2010; Examiner Interview Summary Record for U.S. Appl. No. 11/544,196, dated Dec. 16, 2010; Non Final Office Action for U.S. Appl. No. 11/544,196, dated Jun. 23, 2010; Amendment Response to Final Office Action dated Nov. 27, 2009, for U.S. Appl. No. 11/544,196, submitted on May 7, 2010; Examiner Interview Summary Record for U.S. Appl. No. 11/544,196, dated Feb. 16, 2010; Final Office Action for U.S. Appl. No. 11/544,196, dated Nov. 27, 2009; Examiner Interview Summary Record for U.S. Appl. No. 11/544,196, dated Aug. 6, 2009; Supplemental Amendment Response to Non Final Office Action dated Sep. 2, 2003, for U.S. Appl. No. 11/544,196, submitted on Aug. 3, 2009; Amendment Response to Non Final Office Action dated Sep. 2, 2003, for U.S. Appl. No. 11/544,196, submitted on Jun. 23, 2009; Non Final Office Action for U.S. Appl. No. 11/544,196, dated Feb. 23, 2009; Preliminary Amendment for U.S. Appl. No. 11/544,196, submitted Oct. 6, 2006; Application for U.S. Appl. No. 11/544,196, filed Oct. 6, 2006.
File history for related U.S. Appl. No. 11/545,272, filed Oct. 6, 2006, Inventor D. Bruce Modesitt, including (154 pages total): Terminal Disclaimer for U.S. Appl. No. 11/545,272, submitted Dec. 23, 2010; Amendment Response to Non Final Office Action dated Jun. 23, 2010, for U.S. Appl. No. 11/545,272, submitted on Dec. 23, 2010; Examiner Interview Summary Record for U.S. Appl. No. 11/545,272, dated Dec. 16, 2010; Non Final Office Action for U.S. Appl. No. 11/545,272, dated Jun. 23, 2010; Amendment Response to Final Office Action dated Nov. 25, 2009, for U.S. Appl. No. 11/545,272, submitted on May 7, 2010; Examiner Interview Summary Record for U.S. Appl. No. 11/545,272, dated Feb. 16, 2010; Final Office Action for U.S. Appl. No. 11/545,272, dated Nov. 25, 2009; Examiner Interview Summary Record for U.S. Appl. No. 11/545,272, dated Aug. 3, 2009; Supplemental Amendment Response to Non Final Office Action dated Feb. 18, 2009, for U.S. Appl. No. 11/545,272, submitted on Aug. 3, 2009; Amendment Response to Non Final Office Action dated Feb. 18, 2009, for U.S. Appl. No. 11/545,272, submitted on Jun. 18, 2009; Non Final Office Action for U.S. Appl. No. 11/545,272, dated Feb. 18, 2009; Preliminary Amendment for U.S. Appl. No. 11/545,272, submitted Oct. 6, 2006; Application for U.S. Appl. No. 11/545,272, filed Oct. 6, 2006.
File history for related U.S. Appl. No. 11/544,365, filed Oct. 6, 2006, Inventor D. Bruce Modesitt, including (152 pages total): Terminal Disclaimer for U.S. Appl. No. 11/544,365, submitted Dec. 23, 2010; Amendment Response to Non Final Office Action dated

(56) References Cited

OTHER PUBLICATIONS

Jun. 25, 2010, for U.S. Appl. No. 11/544,365, submitted on Dec. 23, 2010; Examiner Interview Summary Record for U.S. Appl. No. 11/544,365, dated Dec. 16, 2010; Non Final Office Action for U.S. Appl. No. 11/544,365, dated Jun. 25, 2010; Amendment Response to Final Office Action dated Nov. 18, 2009, for U.S. Appl. No. 11/544,365, submitted on May 7, 2010; Examiner Interview Summary Record for U.S. Appl. No. 11/544,365, dated Feb. 16, 2010; Final Office Action for U.S. Appl. No. 11/544,365, dated Nov. 18, 2009; Examiner Interview Summary Record for U.S. Appl. No. 11/544,365, dated Aug. 6, 2009; Supplemental Amendment Response to Non Final Office Action dated Feb. 23, 2009, for U.S. Appl. No. 11/544,365, submitted on Aug. 6, 2009; Amendment Response to Non Final Office Action dated Feb. 23, 2009, for U.S. Appl. No. 11/544,365, submitted on Jun. 22, 2009; Non Final Office Action for U.S. Appl. No. 11/544,365, dated Feb. 23, 2009; Preliminary Amendment for U.S. Appl. No. 11/544,365, submitted Oct. 6, 2006; Application for U.S. Appl. No. 11/544,365, filed Oct. 6, 2006.
File history for related U.S. Appl. No. 11/544,177, filed Oct. 6, 2006, Inventor D. Bruce Modesitt, including (167 pages total): Terminal Disclaimer for U.S. Appl. No. 11/544,177, submitted Mar. 18, 2011; Amendment Response to Non Final Office Action dated Jun. 22, 2010, for U.S. Appl. No. 11/544,177, submitted on Dec. 22, 2010; Terminal Disclaimer for U.S. Appl. No. 11/544,177, submitted Dec. 22, 2011; Non Final Office Action for U.S. Appl. No. 11/544,177, dated Jun. 22, 2010; Amendment Response to Final Office Action dated Nov. 25, 2009, for U.S. Appl. No. 11/544,177, submitted on May 7, 2010; Examiner Interview Summary Record for U.S. Appl. No. 11/544,177, dated Feb. 16, 2010; Final Office Action for U.S. Appl. No. 11/544,177, dated Nov. 25, 2009; Examiner Interview Summary Record for U.S. Appl. No. 11/544,177, dated Aug. 6, 2009; Supplemental Amendment Response to Non Final Office Action dated Feb. 24, 2009, for U.S. Appl. No. 11/544,177, submitted on Aug. 6, 2009; Amendment Response to Non Final Office Action dated Feb. 24, 2009, for U.S. Appl. No. 11/544,177, submitted on Jun. 24, 2009; Non Final Office Action for U.S. Appl. No. 11/544,177, dated Feb. 24, 2009; Preliminary Amendment for U.S. Appl. No. 11/544,177, submitted Oct. 6, 2006; Application for U.S. Appl. No. 11/544,177, filed Oct. 6, 2006.
File history for related application U.S. Appl. No. 11/544,149, filed Oct. 6, 2006, Inventor D. Bruce Modesitt, including (170 pages total): Terminal Disclaimer for U.S. Appl. No. 11/544,149, submitted Mar. 18, 2011; Amendment Response to Non Final Office Action dated Jun. 24, 2010, for U.S. Appl. No. 11/544,149, submitted on Dec. 23, 2010;Terminal Disclaimer for U.S. Appl. No. 11/544,149, submitted Dec. 23, 2011; Non Final Office Action for U.S. Appl. No. 11/544,149, dated Jun. 24, 2010; Amendment Response to Final Office Action dated Dec. 8, 2009, for U.S. Appl. No. 11/544,149, submitted on May 3, 2010; Examiner Interview Summary Record for U.S. Appl. No. 11/544,149, dated Feb. 16, 2010; Final Office Action for U.S. Appl. No. 11/544,149, dated Dec. 8, 2009; Examiner Interview Summary Record for U.S. Appl. No. 11/544,149, dated Aug. 6, 2009; Supplemental Amendment Response to Non Final Office Action dated Feb. 18, 2009, for U.S. Appl. No. 11/544,149, submitted on Aug. 6, 2009; Amendment Response to Non Final Office Action dated Feb. 18, 2009, for U.S. Appl. No. 11/544,149, submitted on Jun. 18, 2009; Non Final Office Action for U.S. Appl. No. 11/544,149, dated Feb. 18, 2009; Preliminary Amendment for U.S. Appl. No. 11/544,149, submitted Oct. 6, 2006; Application for U.S. Appl. No. 11/544,149 as filed on Oct. 6, 2006.
File history for related U.S. Appl. No. 10/888,682, filed Jul. 10, 2004, Inventor D. Bruce Modesitt, including (141 pages total): Supplemental Amendment Response to Final Office Action dated May 6, 2009 for U.S. Appl. No. 10/888,682, submitted on Aug. 28, 2009 Amendment Response to Final Office Action dated May 6, 2009 for U.S. Appl. No. 10/888,682, submitted on Jul. 1, 2009 Final Office Action for U.S. Appl. No. 10/888,682, dated May 6, 2009 Amendment Response to Non Final Office Action dated Jul. 31, 2008 for U.S. Appl. No. 10/888,682, submitted on Nov. 26, 2008 Non Final Office Action for U.S. Appl. No. 10/888,682, dated Jul. 31, 2008 Response to Restriction and Election dated Feb. 15, 2008 for U.S. Appl. No. 10/888,682, submitted on Apr. 30, 2008 Requirement for Restriction and Election for U.S. Appl. No. 10/888,682, dated Feb. 15, 2008 Application for U.S. Appl. No. 10/888,682, filed Jul. 10, 2004.
File history for related U.S. Appl. No. 12/693,395, filed Jan. 25, 2010, Inventor D. Bruce Modesitt, including (61 pages): Amendment Response to Application filed Jan. 25, 2010 for U.S. Appl. No. 12/693,395, submitted on Jan. 25, 2010 Application for U.S. Appl. No. 12/693,395, filed Jan. 25, 2010.
File history for related application U.S. Appl. No. 11/432,982, filed May 12, 2006, Inventor D. Bruce Modesitt, including (128 pages): Examiner Interview Summary Record for U.S. Appl. No. 11/432,982, dated Mar. 14, 2011 Notice Regarding Non-Responsive Amendment for U.S. Appl. No. 11/432,982, dated Jan. 5, 2011 Amendment Response to Non Final Office Action dated Apr. 15, 2010 for U.S. Appl. No. 11/432,982, submitted on Oct. 15, 2010 Non Final Office Action for U.S. Appl. No. 11/432,982, dated Apr. 15, 2010 Amendment Response to Final Office Action dated Jun. 11, 2009 for U.S. Appl. No. 11/432,982, submitted on Aug. 27, 2009 Final Office Action for U.S. Appl. No. 11/432,982, dated Jun. 11, 2009 Amendment Response to Non Final Office Action dated Oct. 8, 2008 for U.S. Appl. No. 11/432,982, submitted on Jan. 6, 2009 Non Final Office Action for U.S. Appl. No. 11/432,982, dated Oct. 8, 2008 Application for U.S. Appl. No. 11/432,982, filed May 12, 2006.
File history for related U.S. Appl. No. 11/544,317, filed Oct. 6, 2006, Inventor D. Bruce Modesitt, including (163 pages): Terminal Disclaimer Decision for U.S. Appl. No. 11/544,317, dated Mar. 15, 2011 Amendment Response to Non Final Office Action dated Jun. 24, 2010 for U.S. Appl. No. 11/544,317, submitted on Dec. 23, 2010 Terminal Disclaimer for U.S. Appl. No. 11/544,317, filed Dec. 23, 2010 Non Final Office Action for U.S. Appl. No. 11/544,317, dated Jun. 24, 2010 Amendment Response to Final Office Action dated Aug. 14, 2009 for U.S. Appl. No. 11/544,317, submitted on Feb. 12, 2010 Final Office Action for U.S. Appl. No. 11/544,317, dated Aug. 14, 2009 Amendment Response to Non Final Office Action dated Jan. 9, 2009 for U.S. Appl. No. 11/544,317, submitted on May 11, 2009 Non Final Office Action for U.S. Appl. No. 11/544,317, dated Jan. 9, 2009 Amendment Response to Application filed on Oct. 6, 2006 for U.S. Appl. No. 11/544,317, submitted on Oct. 6, 2006 Application for U.S. Appl. No. 11/544,317, filed Oct. 6, 2006.
File history for related U.S. Appl. No. 11/788,509, filed Apr. 19, 2007, Inventor D. Bruce Modesitt, including (288 pages): Terminal Disclaimer Decision for U.S. Appl. No. 11/788,509, dated Mar. 21, 2011 Terminal Disclaimer for U.S. Appl. No. 11/788,509, filed Mar. 18, 2011 Terminal Disclaimer Decision for U.S. Appl. No. 11/788,509, dated Mar. 11, 2011 Amendment Response to Non Final Office Action dated Jun. 24, 2010 for U.S. Appl. No. 11/788,509, submitted on Dec. 23, 2010 Terminal Disclaimer for U.S. Appl. No. 11/788,509, filed Dec. 23, 2010 Non Final Office Action for U.S. Appl. No. 11/788,509, dated Jun. 24, 2010 Supplemental Amendment Response to Final Office Action dated Aug. 21, 2009 for U.S. Appl. No. 11/788,509, submitted on Apr. 29, 2010 Amendment Response to Final Office Action dated Aug. 21, 2009 for U.S. Appl. No. 11/788,509, submitted on Feb. 19, 2010 Final Office Action for U.S. Appl. No. 11/788,509, dated Aug. 21, 2009 Amendment Response to Notice Regarding Non-Responsive Amendment dated Apr. 15, 2009 for U.S. Appl. No. 11/788,509, submitted on May 14, 2009 Notice Regarding Non-Responsive Amendment for U.S. Appl. No. 11/788,509, dated Apr. 15, 2009 Amendment Response to Non Final Office Action dated Oct. 29, 2008 for U.S. Appl. No. 11/788,509, submitted on Jan. 6, 2009 Non Final Office Action for U.S. Appl. No. 11/788,509, datled Oct. 29, 2008 Response to PTO Notice to Applicant dated May 15, 2007 for U.S. Appl. No. 11/788,509, submitted on Jul. 16, 2007 PTO Notice to Applicant for U.S. Appl. No. 11/788,509, dated May 15, 2007 Amendment Response to Application as filed on Apr. 19, 2007 for U.S. Appl. No. 11/788,509, submitted on Apr. 19, 2007 Application for U.S. Appl. No. 11/788,509, filed Apr. 19, 2007.
File history for related U.S. Appl. No. 12/467,251, filed May 15, 2009, Inventor D. Bruce Modesitt, including (74 pages): Amendment Response to Application as filed on May 15, 2009 for U.S.

(56) References Cited

OTHER PUBLICATIONS

Appl. No. 12/467,251, submitted on May 15, 2009 Application for U.S. Appl. No. 12/467,251, filed May 15, 2009.
File history for related U.S. Appl. No. 11/873,957, filed Oct. 17, 2007, Inventor D. Bruce Modesitt, et al., including (90 pages): Amendment Response to Notice Regarding Non-Responsive Amendment dated Feb. 7, 2011 for U.S. Appl. No. 11/873,957, submitted on Mar. 2, 2011 Examiner Interview Summary Record for U.S. Appl. No. 11/873,957, dated Feb. 7, 2011 Notice Regarding Non-Responsive Amendment for U.S. Appl. No. 11/873,957, dated Feb. 7, 2011 Amendment Response to Non Final Office Action dated Aug. 2, 2010 for U.S. Appl. No. 11/873,957, submitted on Feb. 2, 2011 Terminal Disclaimer for U.S. Appl. No. 11/873,957, filed Feb. 2, 2011 Non Final Office Action for U.S. Appl. No. 11/873,957, dated Aug. 2, 2010 Application for U.S. Appl. No. 11/873,957, filed Oct. 17, 2007.
File history for related U.S. Appl. No. 12/507,038, filed Jul. 21, 2009, Inventor Michael Drews, et al., including (90 pages): Application for U.S. Appl. No. 12/507,038, filed Jul. 21, 2009.
File history for related U.S. Appl. No. 12/507,043, filed Jul. 21, 2009, Inventor Michael Drews, et al., including (97 pages): Application for U.S. Appl. No. 12/507,043, filed Jul. 21, 2009.
File history for related U.S. Appl. No. 12/780,768, filed May 14, 2010, Inventor Michael Drews, et al., including (97 pages): Application for U.S. Appl. No. 12/780,768, filed May 14, 2010.
File History for related U.S. Appl. No. 12/888,309, filed Sep. 22, 2010, Inventor D. Bruce Modesitt, et al., including ( pages): Application for U.S. Appl. No. 12/888,309, filed Sep. 22, 2010.
File history for related U.S. Appl. No. 13/004,848, filed Jan. 11, 2011, Inventor D. Bruce Modesitt, et al., including (91 pages): Application for U.S. Appl. No. 13/004,848, filed Jan. 11, 2011.
Office Action dated Apr. 13, 2010, for Australian Patent Application No. 2005244834, with a filed of May 12, 2005. (3 pages).
Office Action dated Jun. 3, 2010, for Chinese Patent Application No. 200580023327.X , with a filing date of May 12, 2005, with English translation provided by Chinese associate. (7 pages).
Further Office Action dated Sep. 6, 2010, for Israeli Patent Application No. 179173, with a filed of Jun. 30, 2005, with English translation provided by Israeli associate. (9 pages).
Response to Office Action submitted Jul. 13, 2010, for Israeli Patent Application No. 179173, with a filing date of Jun. 30, 2005. (1 page).
Initial Office Action dated Jan. 25, 2010, for Israeli Patent Application No. 179173, with a filing date of Jun. 30, 2005, with English translation provided by Israeli associate. (5 pages).
Office Action dated Jun. 4, 2010, for Australian Patent Application No. 2005272102, with a filing date of Jun. 30, 2005. (3 pages).
Office Action dated Jun. 4, 2010, for Chinese Patent Application No. 2005800293656, with a filing date of Jun. 30, 2005, with English translation provided by Chinese associate. (10 pages).
European Search Report from European Patent Office for EP application No. EP05787529.6, Applicant Arstasis, Inc., EPO Forms 1507, 1503, and P0459, dated Nov. 5, 2010. (5 pages).
Further Office Action dated May 24, 2010, for Israeli Patent Application No. 180497, with a filing date of May 12, 2005, with English translation provided by Israeli associate. (5 pages).
Response to Office Action submitted May 23, 2010, for Israeli Patent Application No. 180497, with a filing date of May 12, 2005, with English translation provided by Israeli associate. (7 pages).
Initial Office Action dated Jan. 24, 2010, for Israeli Patent Application No. 180497, with a filing date of May 12, 2005, with English translation provided by Israeli associate. (5 pages).
PCT International Search Report and Written Opinion for PCT/US2006/018915, Applicant Arstasis, Inc., Forms PCT/ISA/210 and 237 dated Aug. 20, 2007. (6 pages).
Office Action dated May 22, 2009, for Chinese Patent Application No. 2006800252468, with a filing date of May 12, 2006, with English translation provided by Chinese associate. (7 pages).

PCT International Preliminary Report on Patentability for PCT/US2009/051320, Applicant Arstasis, Inc., Forms PCT/IB/373 and PCT/ISA/237 dated Jan. 25, 2011. (7 pages).
PCT International Search Report and Written Opinion for PCT/US2009/051320, Applicant Arstasis, Inc., Forms PCT/ISA/210, 220, and 237 dated Nov. 6, 2009. (11 pages).
PCT International Search Report and Written Opinion for PCT/US2010/035001, Applicant Arstasis, Inc., Forms PCT/ISA/210, 220, and 237 dated Jul. 19, 2010. (11 pages).
PCT International Search Report and Written Opinion for PCT/US2010/049859, Applicant Arstasis, Inc., Forms PCT/ISA/210, 220, and 237 dated Nov. 5, 2010. (14 pages).
Office Action dated Jan. 24, 2011, for Japanese Patent Application No. 2007-513356, with a filing date of May 12, 2005, and with English translation provided by Japanese associate, (7 pages).
Office Action dated Jan. 24, 2011, for Japanese Patent Application No. 2008-123950, with a filing date of May 12, 2005, and with English translation provided by Japanese associate, (4 pages).
Response to Office Action submitted Oct. 18, 2010, for Chinese Patent Application No. 2005800293656, with English instructions to respond provided to Chinese associate, (27 pages).
Office Action dated Feb. 14, 2011, for European Patent Application No. 05787529.6, with a filing date of Jun. 30, 2005, (15 pages).
Office Action dated Dec. 8, 2010, for Japanese Patent Application No. 2007-0520363, with a filing date of Jun. 30, 2005, and with English translation provided by Japanese associate, (5 pages).
Response to Office Action submitted Nov. 6, 2010, for Chinese Patent Application No. 2006800252468, with English instructions to respond provided to Chinese associate. (29 pages).
International Search Report and Written Opinion, International Application No. PCT/US13/42743, dated Oct. 24, 2013 (11 pages).
Office Action dated Jan. 14, 2014 for Israeli Application No. 210754 (5 pages).
Office Action dated Jan. 14, 2014 for Israeli Application No. 210755 (4 pages).
International Search Report and Written Opinion,International PCT Application No. PCT/US2013/052926, International Filing Date of Jul. 31, 2013; dated Nov. 26, 2013. (9 pages).
Second Office Action for Chinese Patent Application No. 200980135885.3, dated Sep. 26, 2013. (6 pages).
Search Report dated Nov. 30, 2012 for European Application No. EP12156932.1. (9 pages).
Office Action dated May 24, 2012 for Canadian Application No. 2566743. (4 pages).
Further Office Action dated Mar. 8, 2013 for Canadian Application No. 2566743. (5 pages).
Further Office Action dated Dec. 23, 2013 for Canadian Application No. 2566743. (6 pages).
Decision of Rejection and Translation dated Jul. 4, 2012 for Chinese Application No. 200580023327_X. (6 pages).
Office Action dated May 10, 2013 for Chinese Application No. 200580023327_X. (5 pages).
Further Office Action dated Nov. 25, 2013 for Chinese Application No. 200580023327_X. (3 pages).
Official Communication dated Nov. 26, 2012 for European Application No. 05747814.1. (5 pages).
Supplementary Search Report dated Jul. 23, 2012 for European Application No. 05747814.1. (4 pages).
Office Action dated Aug. 27, 2013 for Israeli Application No. 179173 (7 pages).
Examination Report dated Feb. 27, 2012 for European Application No. 08011884.7. (3 pages).
Office Action dated Sep. 10, 2012 for Japanese Application No. 2008-123950 (6 pages).
Notice of Final Rejection dated Nov. 17, 2011 for Japanese Application No. 2008-123950 (5 pages).
Partial Search Report dated Aug. 12, 2013 for European Application No. 12156932.1 (6 pages).
Search Report dated Nov. 12, 2013 for European Application No. 12156932.1 (9 pages).
Examination Report dated Nov. 1, 2012 for Australian Application No. 2012200175. (4 pages).

(56) References Cited

OTHER PUBLICATIONS

Office Action dated Nov. 20, 2013 for Japanese Application No. 2012-061872 (6 pages).
Office Action dated May 23, 2012 for Canadian Application No. 2573065. (3 pages).
Office Action dated Feb. 5, 2013 for Israeli Application No. 187109 (5 pages).
Office Action dated Dec. 28, 2012, for Chinese Patent Application No. 2005800293656, with a filing date of Jun. 30, 2005, with English translation provided by Chinese associate. (6 pages).
Office Action dated 22 Apr. 2013, for Chinese Patent Application No. 2005800293656, with a filing date of Jun. 30, 2005, with English translation provided by Chinese associate. (6 pages).
Supplementary Search Report dated Nov. 5, 2010 for European Application No. 05787529.6. (5 pages).
Official Communicaiton dated Feb. 14, 2011 for European Application No. 05787529.6. (4 pages).
Examination Report dated Sep. 11, 2012 for Australian Application No. 2012201140. (4 pages).
Examination Report dated Mar. 16, 2011 for Australian Application No. 2006247355. (4 pages).
Examination Report No. 2 dated Oct. 25, 2012 for Australian Application No. 2006247355. (3 pages).
Office Action dated Jan. 16, 2013 for Canadian Application No. 2607387. (2 pages).
Notice of Rejection (Translation) dated Nov. 13, 2012 for Japanese Application No. 2010-101185. (3 pages).
First Office Action dated Jan. 7, 2013, for Chinese Patent Application No. 200980135885.3, with English translation provided by Chinese associate. (6 pages).
Second Office Action dated Sep. 26, 2013, for Chinese Patent Application No. 200980135885.3, with English translation provided by Chinese associate. (12 pages).
Notice of Rejection and English Translation dated Sep. 2, 2013 for Japanese Application No. 2010-520145. (4 pages).
Office Action dated Feb. 2, 2014 for Israeli Application No. 216263 (5 pages).
"International Search Report and Written Opinion", International Application No. PCT/US13/42743, dated Oct. 24, 2013,.
Extended European Search Report dated Jul. 31, 2015, European Patent Application No. 14196344.7, (5 pages).
First Office Action (English Translation), Chinese Patent Application No: 201080052596.X, dated Mar. 5, 2014, (17 pages).
Extended European Search Report dated Jan. 4, 2016, European Patent Application No. 13793912.0, (9 pages).
Examiner's Report dated Jan. 7, 2019 , Canadian Application No. 2874671 , (3 pages).
First Examination Report dated Nov. 9, 2018, Australian Patent Application No. 2017251835 , (4 pages).
First Office Action dated May 2, 2018 with English Translation, Israel Patent Application No: 235845 , (8 pages).

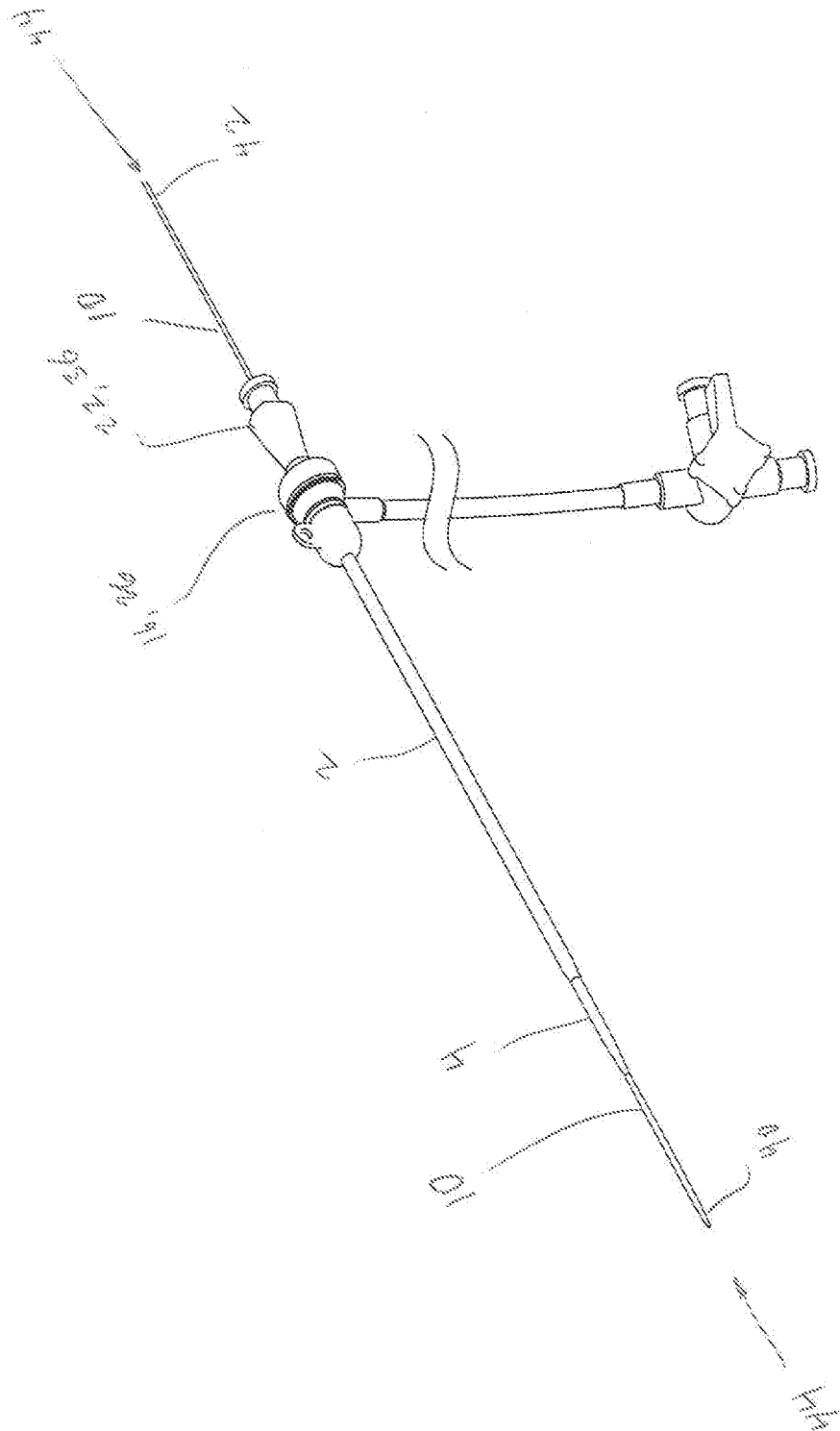

VASCULAR ACCESS CONFIGURATION

RELATED APPLICATION DATA

The present application is a continuation of U.S. patent application Ser. No. 15/238,668, filed on Aug. 16, 2016, which is a continuation of U.S. patent application Ser. No. 14/940,109, filed on Nov. 12, 2015, which is a continuation of U.S. patent application Ser. No. 13/902,579, filed on May 24, 2013, which claims the benefit under 35 U.S.C. § 119 to U.S. Provisional Application Ser. No. 61/652,104, filed May 25, 2012. The foregoing applications are hereby incorporated by reference into the present application in their entirety.

FIELD OF THE INVENTION

The present invention relates generally to vascular access systems and techniques, and more particularly to configurations for providing and/or facilitating elongate instrument access across a vascular wall with minimal disruption to surrounding tissue structures.

BACKGROUND

A number of diagnostic and interventional vascular procedures are now performed translumenally, where an elongate instrument such as a catheter is introduced to the vascular system at a convenient access location—such as the femoral, brachial, or subclavian arteries—and guided through the vascular system to a target location to perform therapy or diagnosis. When vascular access is no longer required, the catheter and other vascular access devices must be removed from the vascular entrance and bleeding at the puncture site must be stopped. One common approach for providing hemostasis is to apply external force near and upstream from the puncture site, typically by manual compression. This method is time-consuming, frequently requiring one-half hour or more of compression before hemostasis. This procedure is uncomfortable for the patient and frequently requires administering analgesics. Excessive pressure can also present the risk of total occlusion of the blood vessel, resulting in ischemia and/or thrombosis. After hemostasis is achieved by manual compression, the patient is required to remain recumbent for six to eighteen hours under observation to assure continued hemostasis. During this time bleeding from the vascular access wound can restart, potentially resulting in major complications. These complications may require blood transfusion and/or surgical intervention.

Bioabsorbable fasteners have also been used to stop bleeding. Generally, these approaches rely on the placement of a thrombogenic and bioabsorbable material, such as collagen, at the superficial arterial wall over the puncture site. This method generally presents difficulty locating the interface of the overlying tissue and the adventitial surface of the blood vessel. Implanting the fastener too far from the desired location can result in failure to provide hemostasis. If, however, the fastener intrudes into the vascular lumen, thrombus can form on the fastener. Thrombus can embolize downstream and/or block normal blood flow at the thrombus site. Implanted fasteners can also cause infection and autoimmune reactions/rejections of the implant.

Suturing methods also have used to provide hemostasis after vascular access. The suture-applying device is introduced through the tissue tract with a distal end of the device located at the vascular puncture. Needles in the device draw suture through the blood vessel wall on opposite sides of the punctures, and the suture is secured directly over the adventitial surface of the blood vessel wall to close the vascular access wound. Generally, to be successful, suturing methods need to be performed with a precise control. The needles need to be properly directed through the blood vessel wall so that the suture is well anchored in tissue to provide for tight closure. Suturing methods also require additional steps for the physician.

In view of the deficiencies of the above methods and devices, a new generation of "self-sealing" closure devices and methods has been developed to avoid the need for implantation of a prosthesis member, and also to minimize the steps and time required for closure of the vascular site. Such self-sealing configurations are available, for example, from Arstasis, Inc., of Redwood City, Calif. under the tradename Axera™, and are described in publications such as U.S. Pat. Nos. 8,083,767, 8,012,168, 8,002,794, 8,002,793, 8,002,792, 8,002,791, 7,998,169, and 7,678,133, each of which is incorporated by reference herein in its entirety.

With self-sealing and other configurations of closure devices, it may be desirable to achieve vascular access with relatively small instruments before dilation up to larger working lumens for subsequent diagnostic or interventional steps. For example, rather than starting with a Seldinger access technique wherein a needle and guidewire set configured to place a conventional 0.035" diameter guidewire are utilized, a self-sealing access technique may be employed to place a much smaller guidewire, such as an 0.018" diameter guidewire. With a relatively small guidewire, such as an 0.018" diameter guidewire, in place by the Seldinger technique, a subsequent process step may be to install an introducer catheter assembly, generally comprising an introducer catheter defining an introducer lumen, and a dilator member configured to fit with in the introducer lumen. The dilator member generally will define its own dilator member lumen through which the guidewire may be threaded, to facilitate an "over-the-wire" installation of the distal portions of the introducer catheter and dilator member into the vascular lumen.

One of the challenges with an over-the-wire installation of a conventional introducer-dilator assembly over a relatively small guidewire, such as an 0.018" diameter guidewire, is that many readily available off-the-shelf introducer-dilator sets are configured to fit more conventional guidewire diameters through the dilator member lumen, such as diameters in the range of 0.035 inches. The geometric mismatch between a 0.018" diameter guidewire and a distal end of a dilator member sized for a 0.035" diameter guidewire, for example, can result in what may be termed an "annular gap" that may form a mechanical edge at the interface between these structures, and insertion of this gap or edge relative to the vascular tissue to place the dilator member and associated introducer catheter distal tips within the vascular lumen may result in unwanted localized tissue trauma, heightened insertion forces, and undesirable localized stress concentrations on portions of the guidewire, dilator member, and/or introducer catheter. There is a need to address this challenge so that conventionally-sized dilator-introducer assemblies, such as those designed for 0.035" diameter guidewires, may be more optimally utilized with relatively small guidewires, such as those having diameters in the range of 0.018 inches, which may be desirable with procedures such as self-sealing vascular access and closure procedures.

SUMMARY

One embodiment is directed to a system for creating translumenal vascular access, comprising: a dilator-introducer assembly comprising a dilator member having proximal and distal ends and defining a dilator lumen therethrough, and an introducer member having proximal and distal ends and defining an introducer lumen therethrough, wherein the introducer lumen is defined by an inner diameter profile sized to accommodate insertion of one or more portions of the dilator member; a guidewire having an outer shape defined by a guidewire outer diameter profile; and a dilator adaptor having proximal and distal ends and defining a dilator adaptor lumen therethrough, wherein the dilator adaptor lumen is defined by an inner diameter profile sized to accommodate insertion of one or more portions of the guidewire, and wherein the dilator adaptor is further defined by an outer diameter profile sized to accommodate at least partial insertion of the proximal end of the dilator adaptor into the dilator member lumen; wherein the guidewire may be advanced at least in part through the dilator adaptor lumen, the dilator adaptor may be advanced at least in part through the dilator member lumen, and the dilator member may be advanced at least in part through the introducer lumen to form an instrument assembly capable of forming substantially atraumatic outer shape profile configuration defined by longitudinally sequential increases in overall outer diameter from exposed distal ends of the guidewire, dilator adaptor, dilator member, and introducer. A maximum outer diameter of the guidewire may be substantially smaller than a minimum inner diameter of the dilator member. Without the dilator adaptor interposed between the guidewire and dilator member, an annular gap may be defined at the intersection of the guidewire and a distal end of the dilator member. The maximum outer diameter of the guidewire may be at least about 25% smaller than the minimum inner diameter of the dilator member. The maximum outer diameter of the guidewire may be about 0.018 inches. The minimum inner diameter of the dilator member may be between about 0.035 inches and about 0.040 inches. The dilator adaptor inner and outer diameter profiles may be configured to substantially make up the difference in fit between the guidewire and dilator member. The dilator adaptor may have a minimum inner diameter of about 0.018 inches, and a maximum outer diameter of about 0.050 inches. The introducer member distal end may have a tapered geometry with an outer diameter minimum at its distal tip. The dilator member distal end may have a tapered geometry with an outer diameter minimum at its distal tip. The distal end of the dilator adaptor may have a tapered geometry with an outer diameter minimum at its distal tip. At least a portion of the dilator adaptor may have a proximally tapered geometry with an outer diameter minimum located adjacent its proximal end. A friction fit may be formed between the proximally tapered geometry of the dilator adaptor and the dilator member lumen of the dilator member when loading the dilator adaptor into the dilator member lumen. The proximally tapered geometry may be selected such that one size of dilator adaptor can form a friction fit with a range of dilator member lumen geometries. The dilator adaptor, when viewed from distal end to proximal end, may comprise a distal section with a substantially constant outer diameter for a distal section length, tapering up to a midsection with a substantially constant outer diameter for a midsection length, tapering down to a proximal section with a substantially constant outer diameter for a proximal section length, ending in the proximal end. The substantially constant outer diameter of the proximal section may be greater than that of the distal section and less than that of the midsection. Each of the distal section, midsection, and proximal sections may have a substantially homogeneous inner diameter defining the dilator adaptor lumen. The maximum outer diameter of the guidewire may be at least about 0.01 inches smaller than the minimum inner diameter of the dilator member. The dilator adaptor may comprise a polymer selected from the group consisting of: polyethylene terepthalate, polyethylene, high density polyethylene, polypropylene, polytetrafluoroethylene, expanded polytetrafluoroethylene, poly (ethylene-co-vinyl acetate), poly(butyl methacrylate), and co-polymers thereof.

BRIEF DESCRIPTION OF THE DRAWINGS

FIG. 2G illustrates one aspect of a vascular access configuration in accordance with the present invention wherein a relatively small guidewire may be utilized in concert with a conventionally-sized dilator-introducer assembly.

FIG. 2I illustrates one aspect of a vascular access configuration in accordance with the present invention wherein a relatively small guidewire may be utilized in concert with a conventionally-sized dilator-introducer assembly.

DETAILED DESCRIPTION

Figure 1A:
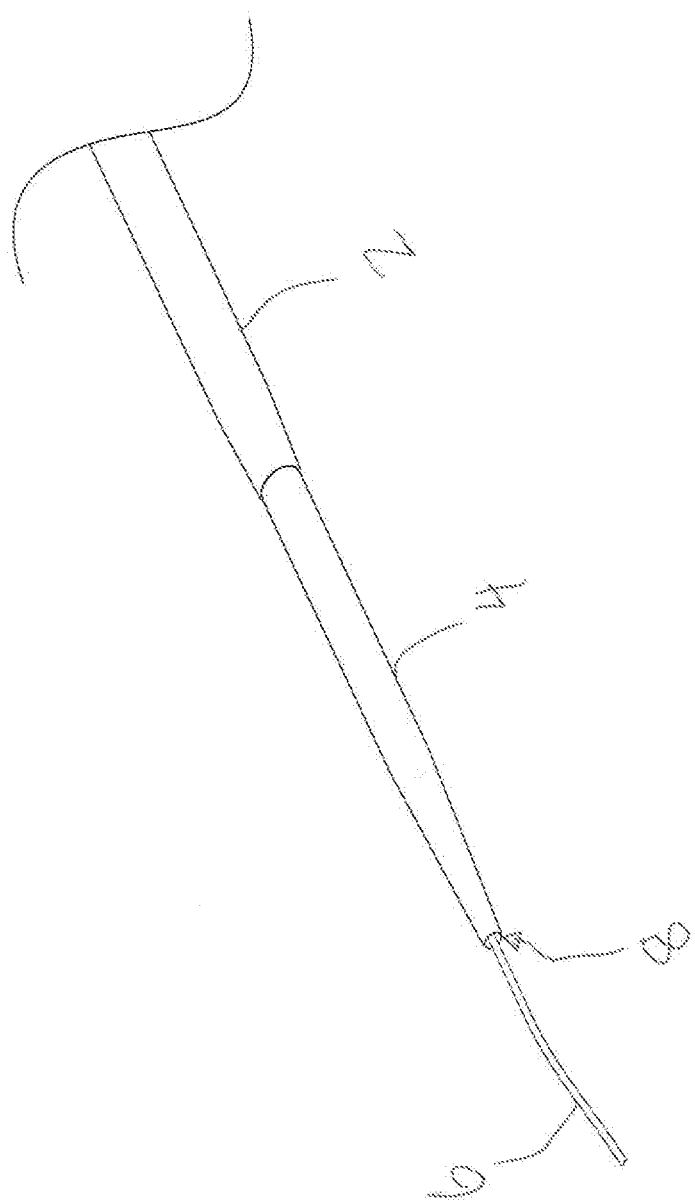
FIG. 1A illustrates a geometric misfit scenario wherein a relatively small guidewire is interfaced with a conventionally-sized dilator-introducer assembly.
Figure 1B:
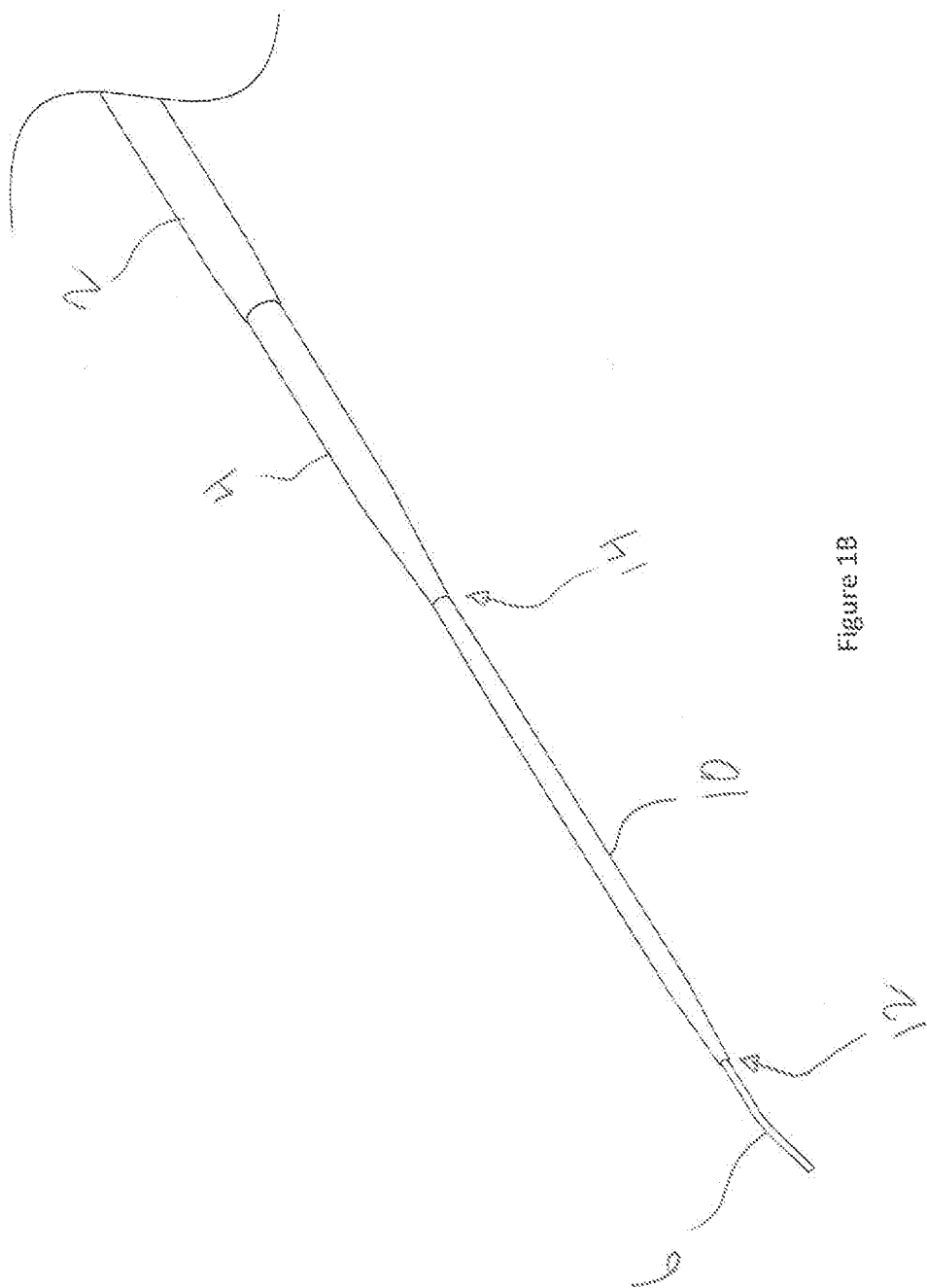
FIG. 1B illustrates an assembly featuring a dilator adaptor to address a geometric misfit scenario such as that depicted in FIG. 1A.

Referring to FIG. 1A, a geometric mismatch scenario is depicted wherein a relatively small guidewire (6), such as a guidewire having a diameter in the range of 0.018 inches, is being utilized in concert with a conventionally-sized dilator-introducer assembly comprising a dilator member (4) coupled through an introducer catheter (2). The dilator member (4) may define a lumen therethrough which has a diameter sized for larger guidewires, in the range of 0.035 inches. As shown in FIG. 1A, and as described above, the geometric mismatch between the guidewire (6) and the inner diameter of the dilator member (4) creates an annular gap (8) or step in geometry, which may unfavorably affect the function of the overall apparatus relative to the nearby pertinent tissue structures. Referring to FIG. 1B, with an appropriate sized and shaped tubular dilator adaptor (10) intercoupled between the dilator member (4) and guidewire (6), the mismatch issue may be substantially, if not completely, mitigated, to produce a desired closely-toleranced fit at the junction (12) between the guidewire (6) and adaptor (10), and at the junction (14) between the adaptor (10) and the dilator member (4).

Referring to FIGS. 2A-2I, various aspects of a vascular access system and procedure related thereto are illustrated. FIGS. 3 and 4 illustrate in a flowchart fashion various embodiments of medical procedures involving such vascular access technology.

Figure 2A:
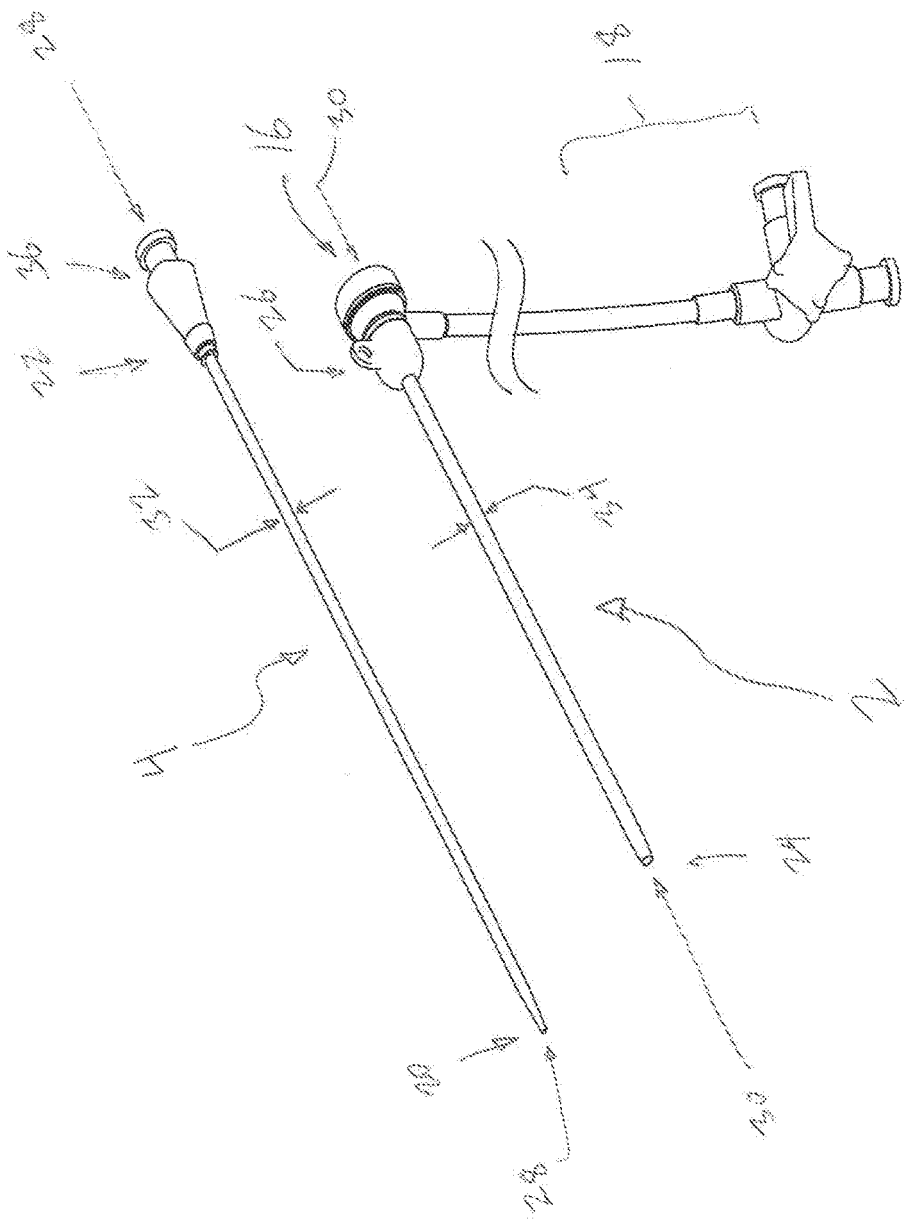
FIG. 2A illustrates one aspect of a vascular access configuration in accordance with the present invention wherein a relatively small guidewire may be utilized in concert with a conventionally-sized dilator-introducer assembly.
Figure 2B:
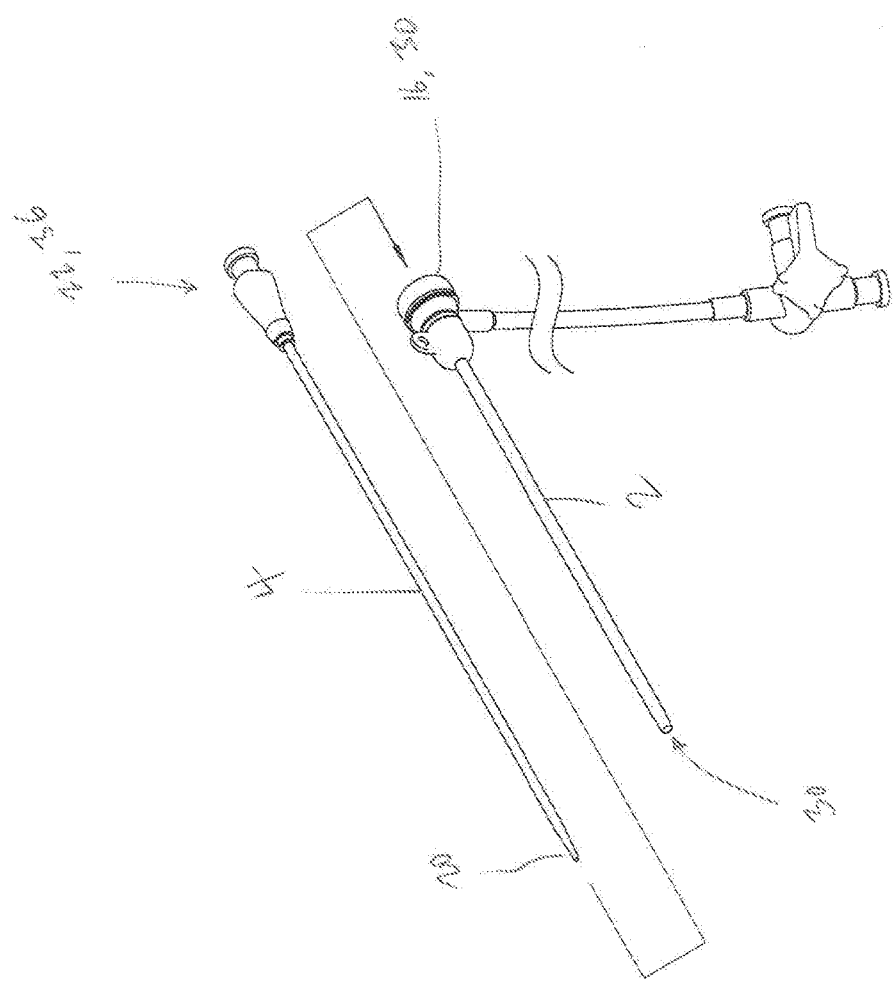
FIG. 2B illustrates one aspect of a vascular access configuration in accordance with the present invention wherein a relatively small guidewire may be utilized in concert with a conventionally-sized dilator-introducer assembly.
Figure 2C:
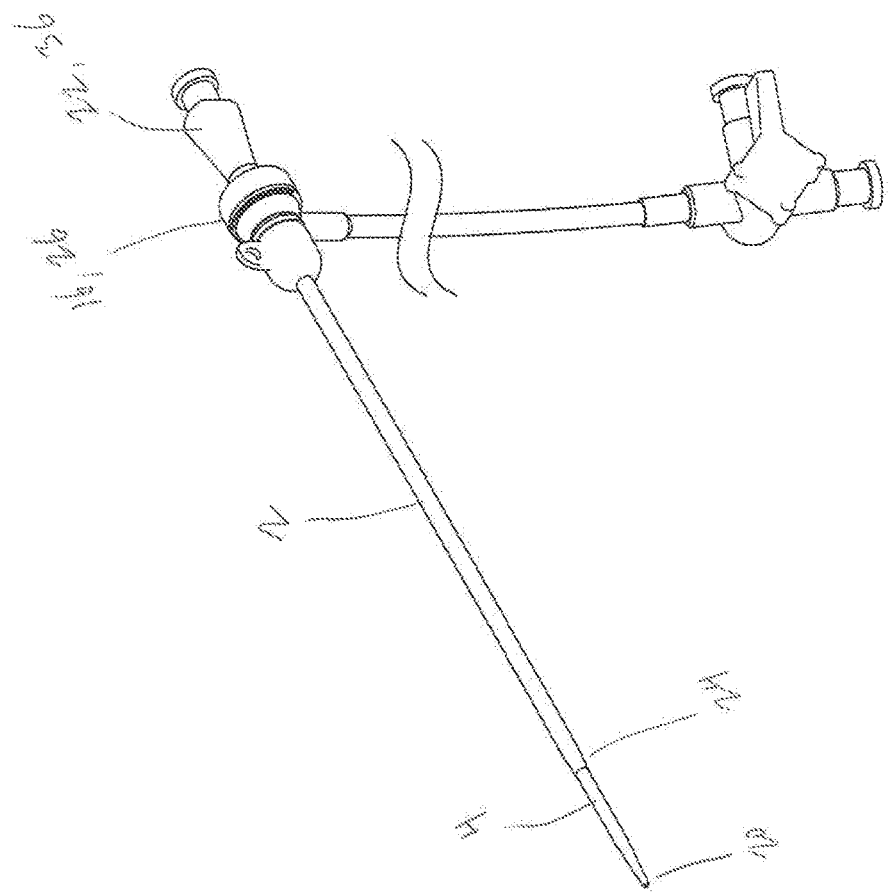
FIG. 2C illustrates one aspect of a vascular access configuration in accordance with the present invention wherein a relatively small guidewire may be utilized in concert with a conventionally-sized dilator-introducer assembly.
Figure 2D:
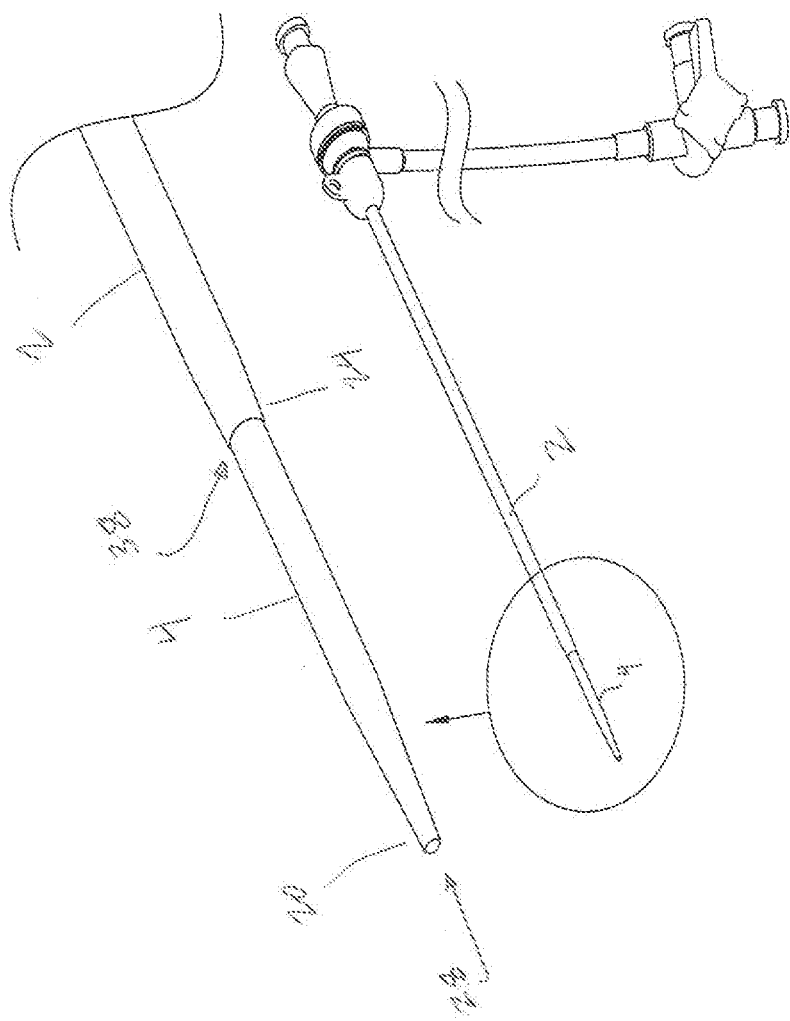
FIG. 2D illustrates one aspect of a vascular access configuration in accordance with the present invention wherein a relatively small guidewire may be utilized in concert with a conventionally-sized dilator-introducer assembly.

Referring to FIG. 2A, a conventional dilator member/introducer catheter set is depicted in a disassembled form, comprising a dilator member (4) having proximal (22) and distal (20) ends, a lumen (28) defined therethrough, and a fitting (36) proximally to assist with manipulating and coupling the dilator member (4). The conventional dilator member/introducer catheter set also comprises an introducer catheter or introducer sheath (2) having proximal (26) and distal (24) ends, a lumen (30) therethrough, and a proximal valve assembly (16), to assist with preventing leaks that may otherwise occur through the lumen (30) and around small instruments, such as the dilator member (4) or other diagnostic and/or interventional tools, which may be passed through the lumen (30) and valve (16). Typical dilator member/introducer catheter sets for vascular access, such as those available from providers such as Boston Scientific Corporation, Covidien, Inc., or St. Jude Medical, Inc., are designed to have outer introducer catheter diameters (34) in the range of about 6 French, and have inner dilator member lumen diameters of between about 0.035" and about 0.038". The outer diameter (32) of the dilator member (4) typically is configured to be easily slideable through the lumen (30) of the introducer (2), without significant leakage between the two elongate bodies when assembled. Referring to FIG. 2B, the distal end (20) of the dilator (4) may be advanced through the proximal end valve fitting (16) of the introducer catheter (2) and into the lumen (30) of the introducer catheter (2), to form an assembly as shown in FIGS. 2C and 2D, wherein the distal end (20) of the dilator member (4) may be configured to have a tapered geometry and to extend distally past the distal end (24) of the introducer catheter (2), which also may have a tapered distal geometry. Preferably the fit (38) at the interface between the dilator member (4) and introducer catheter (2) is manufactured to be closely toleranced by the manufacturer of the dilator/introducer set, as described above.

Figure 2E:
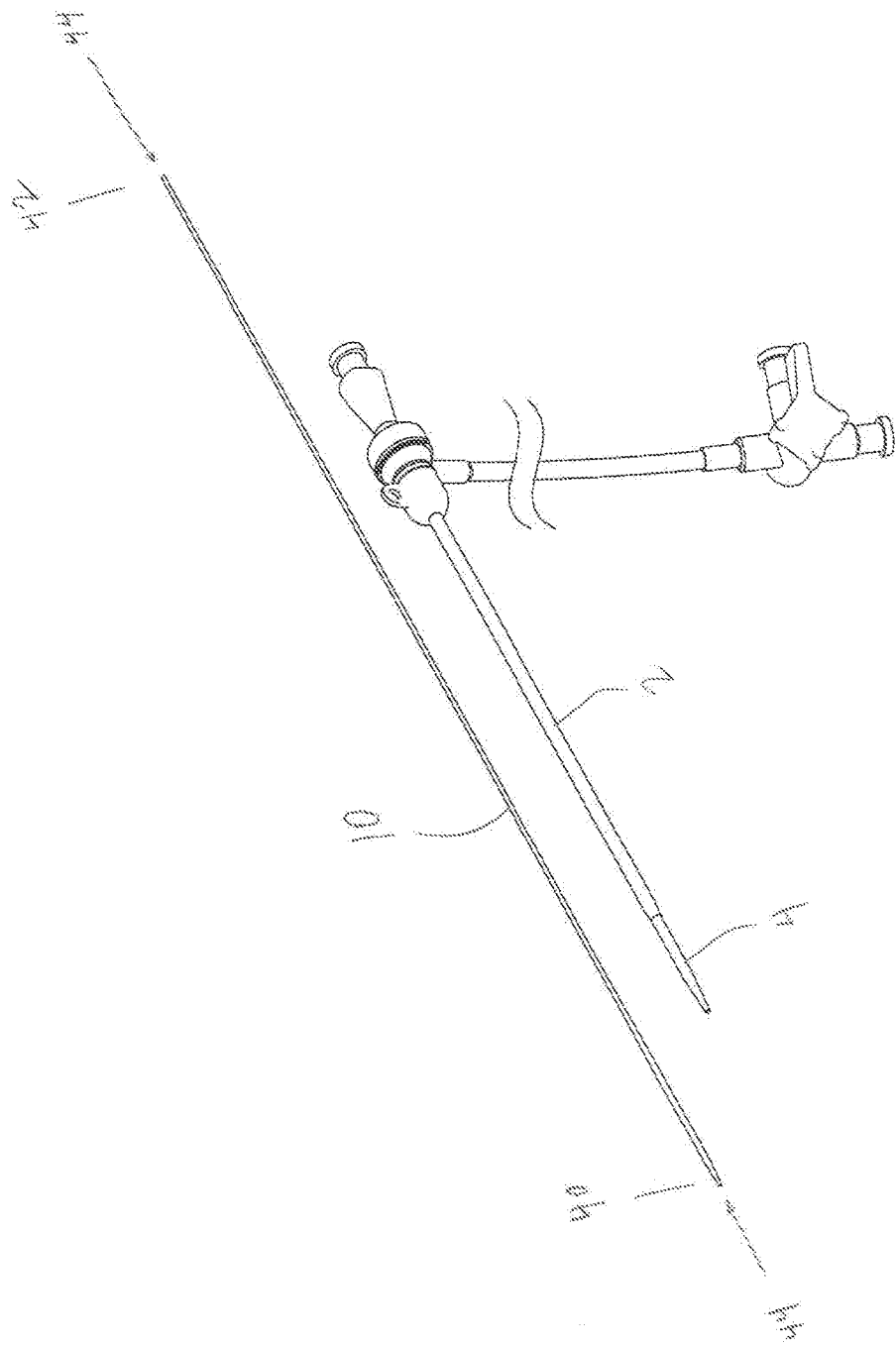
FIG. 2E illustrates one aspect of a vascular access configuration in accordance with the present invention wherein a relatively small guidewire may be utilized in concert with a conventionally-sized dilator-introducer assembly.
Figure 2F:
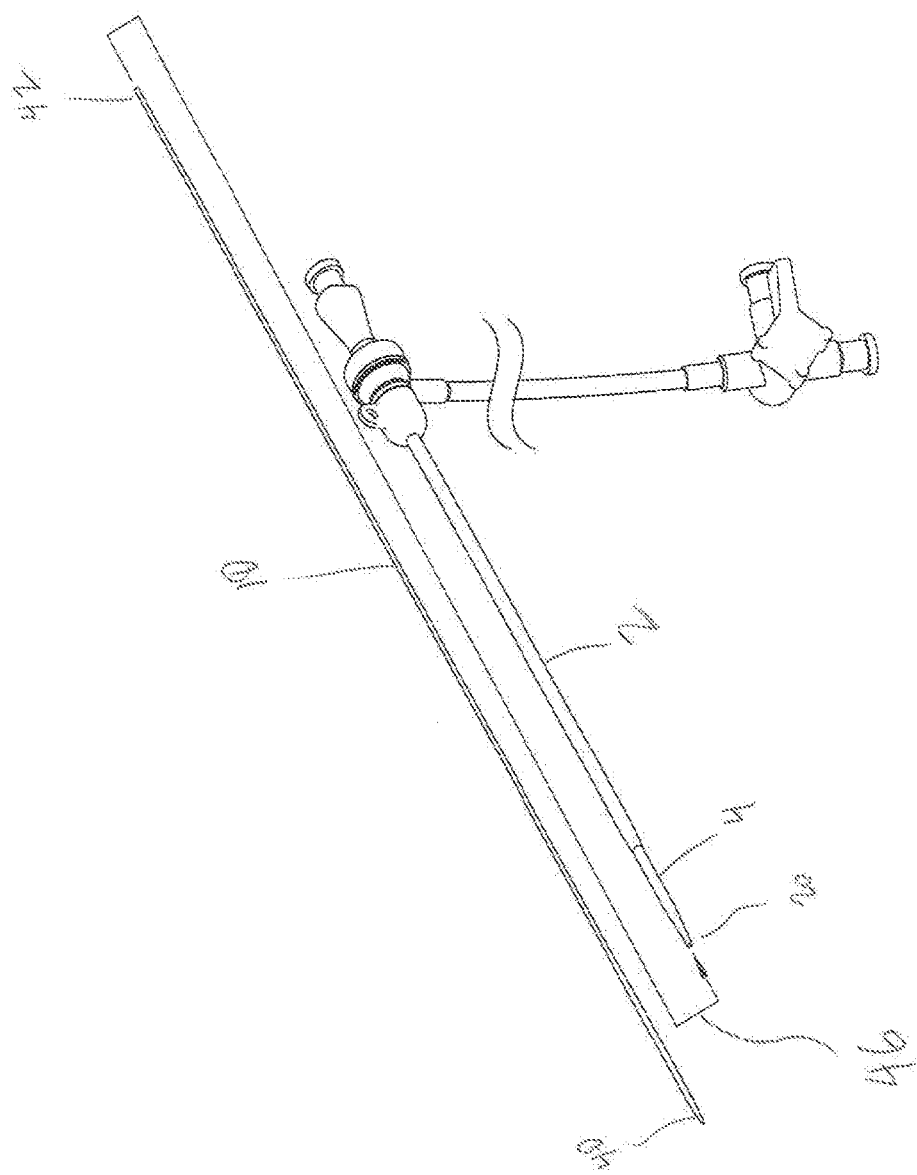
FIG. 2F illustrates one aspect of a vascular access configuration in accordance with the present invention wherein a relatively small guidewire may be utilized in concert with a conventionally-sized dilator-introducer assembly.

Referring to FIG. 2E, in a scenario wherein a relatively small guidewire, such as one in the range of 0.018 inches, is to be utilized in concert with a conventionally-sized dilator/introducer set, such as one having a dilator member lumen diameter of about 0.035 inches, a tubular dilator adaptor member (10) may be added to an assembly to mitigate the geometric mismatch. Generally the dilator adaptor (10) has proximal (42) and distal (40) ends and comprises a small lumen (44) defined therethrough to accommodate passage of a small instrument such as a guidewire. As shown in FIG. 2F, in one embodiment, the dilator adaptor (10) is configured to be inserted proximal end (42) first into the distal end (20) of the dilator member (4), and this assembly may occur before or after the dilator member is assembled into the working lumen of the introducer catheter (2). Referring to FIG. 2G, a resulting assembly is depicted, with the dilator adaptor (10) inserted through the working lumen of the dilator member (4), which is inserted through the working lumen of the introducer catheter (2). A small working lumen (44) is maintained through the dilator adaptor (10) to accommodate passage of a guidewire or other small instrument.

Preferably at least one portion of the proximal end geometry of the dilator adaptor (10) comprises a proximal taper (tapering to smaller outer diameter as one measures incrementally closer to the proximal end of the dilator adaptor) which is configured to interface with the inner lumen geometry of the working lumen of the associated dilator member (4) in such a manner that the dilator adaptor (10) may be pushed up into the distal end of the dilator member (4) until a friction fit is established. Preferably the proximal taper geometry of the dilator adaptor (10) is configured to not only accommodate one guidewire/dilator mismatch scenario (i.e., such as one wherein an 0.018" outer diameter guidewire is to be utilized with a dilator member having an inner lumen diameter of about 0.035"), but also a substantially broad range of mismatch scenarios (including one wherein an 0.018" outer diameter guidewire is to be utilized with a dilator member having an inner lumen diameter of about 0.038", as well as a myriad of other mismatch scenarios which may be greater in mismatch dimensions).

Figure 2H:
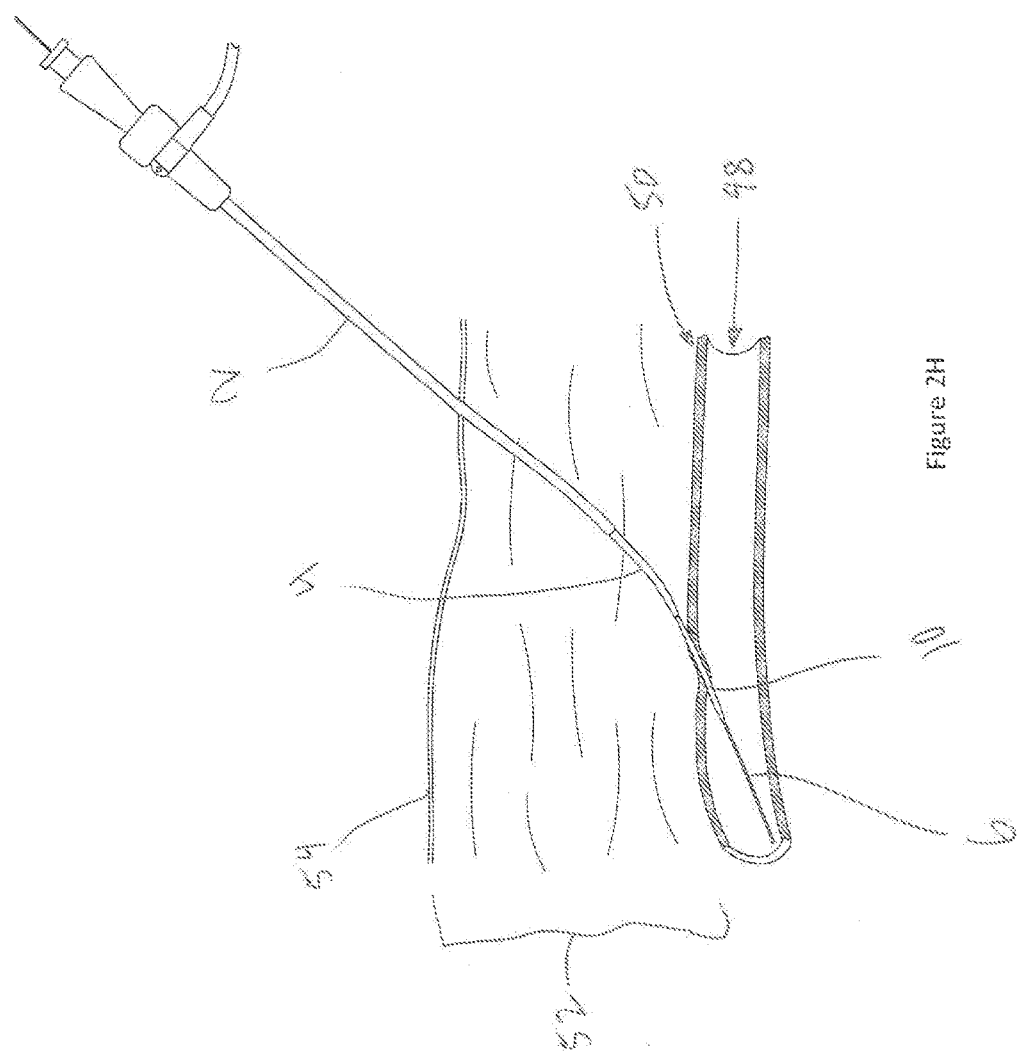
FIG. 2H illustrates one aspect of a vascular access configuration in accordance with the present invention wherein a relatively small guidewire may be utilized in concert with a conventionally-sized dilator-introducer assembly.
Figure 21:
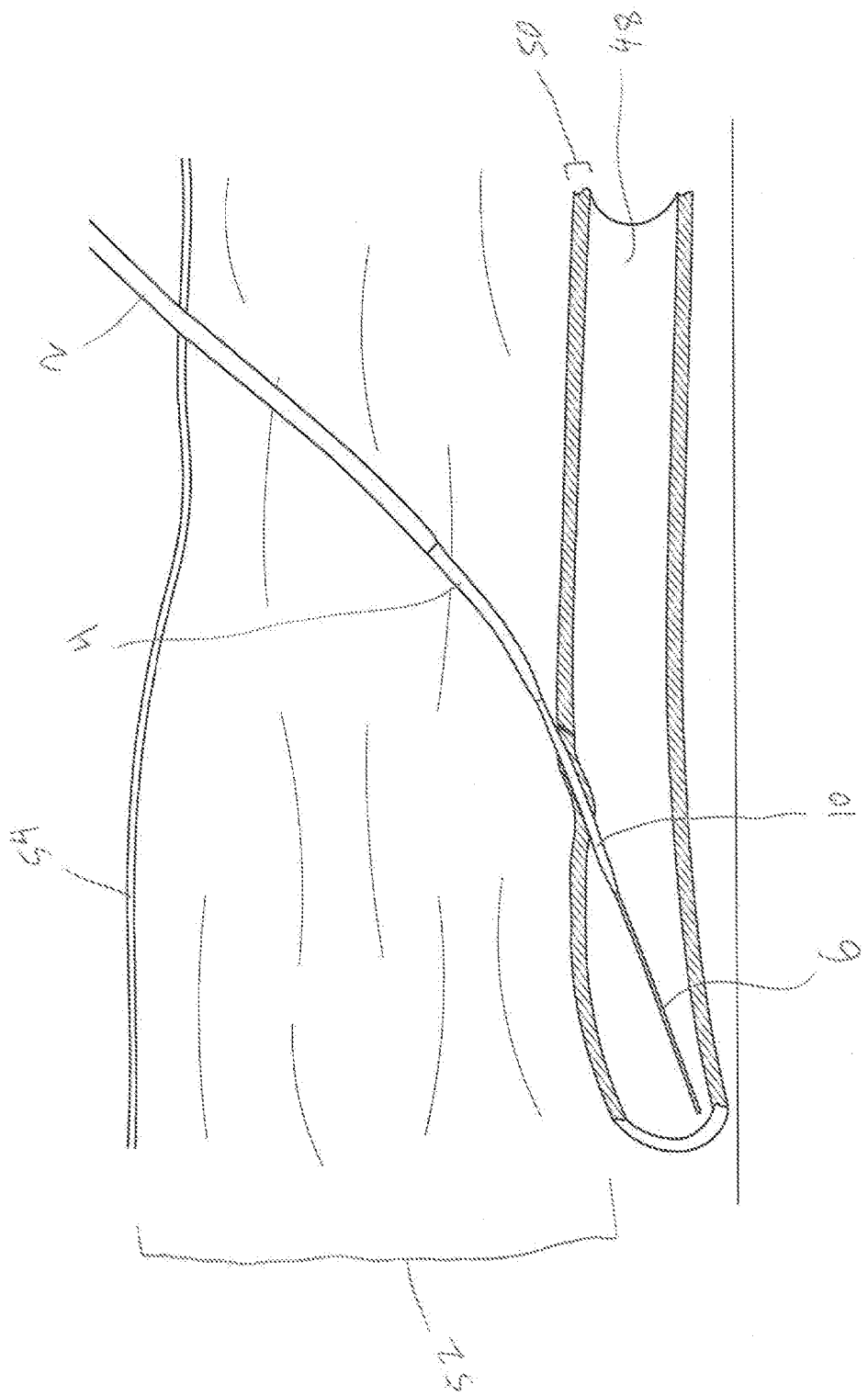

Referring to FIG. 2H, in practice, with a guidewire (6) already installed into a position wherein the distal end of the guidewire extends into a blood vessel lumen (48), and the remainder of the guidewire (10) extends proximally across the vessel wall (50), across other related tissue structures (52), and across the skin (54) of the patient, to extend proximally, generally outside of the patient, an assembly of the dilator adaptor (10), dilator member (4), and introducer catheter (2) may be advanced in an "over-the-wire" technique to place at least a portion of such assembly within the vascular lumen (48). A closer view is presented in FIG. 2I. The assembly may be further advanced until the distal end of the introducer catheter is positioned within the vascular lumen (48), after which the dilator member (4) and dilator adaptor (10) may be withdrawn proximally to make room for other diagnostic and/or interventional tools, such as catheters, imaging devices, and prostheses such as stents which may be passed through the working lumen of the introducer. Subsequently, the tools may with withdrawn, as well as the guidewire and introducer sheath, to complete closure of the trans-vascular access port or wound. As described above, in one embodiment, the trans-vascular access point across the vessel wall (50) may be configured to be a self-sealing access point, which is designed to self-seal after withdrawal of the pertinent instrumentation.

Figure 3A:
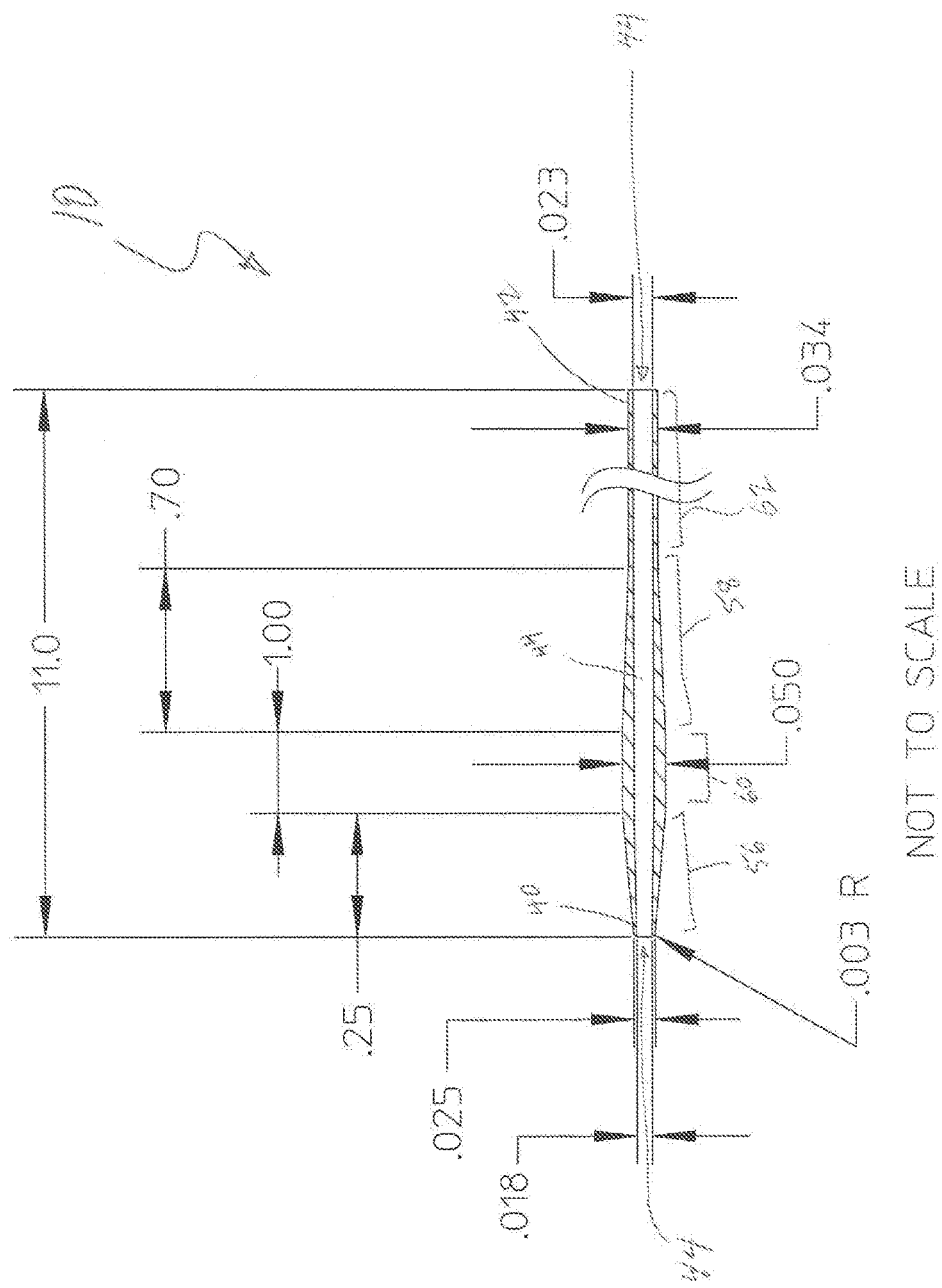
FIG. 3A illustrates a longitudinal cross sectional view of one embodiment of a dilator adaptor in accordance with the present invention.
Figure 4:
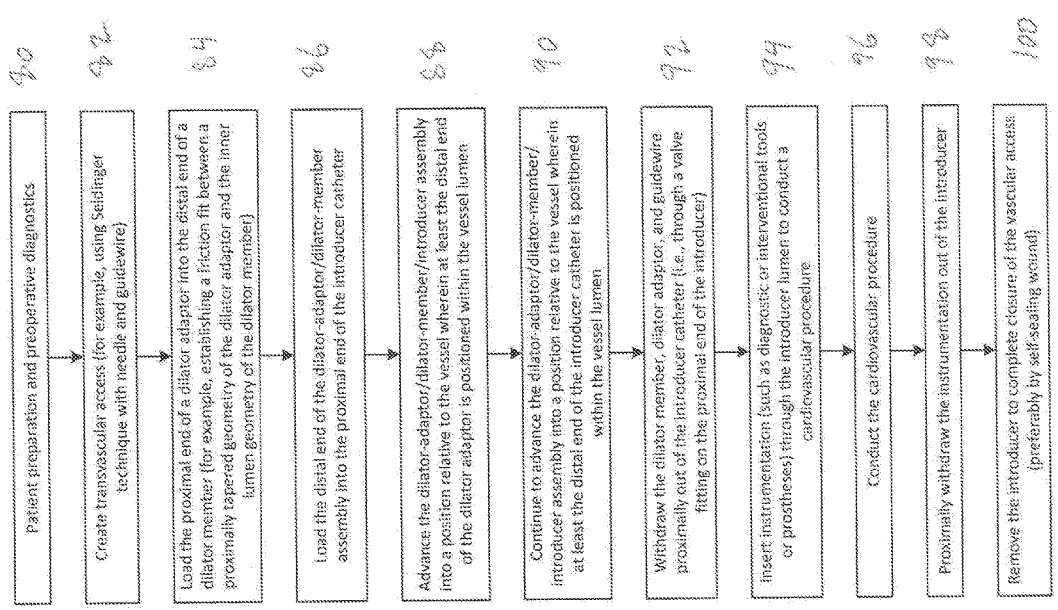
FIG. 4 illustrates a technique conducting a procedure involving a vascular access configuration in accordance with the present invention wherein a relatively small guidewire may be utilized in concert with a conventionally-sized dilator-introducer assembly.

Referring to FIG. 3A, a longitudinal cross sectional view of one embodiment of a dilator adaptor (10) is depicted with dimensions in inches. The most distal portion starting from the distal end (40) may comprise a tapered geometry (56) to ultimately assist with pushing deployment into the pertinent tissue structures. A mid-portion (60) may have a substantially homogeneous outer diameter for a given length. Next a proximally tapered portion (58) may assist with establishing a friction fit with an associated inner lumen geometry of a dilator member, as described above. A most proximal portion (62) up to the proximal end (42) may have a substantially constant outer diameter for a given length.

Figure 3B:
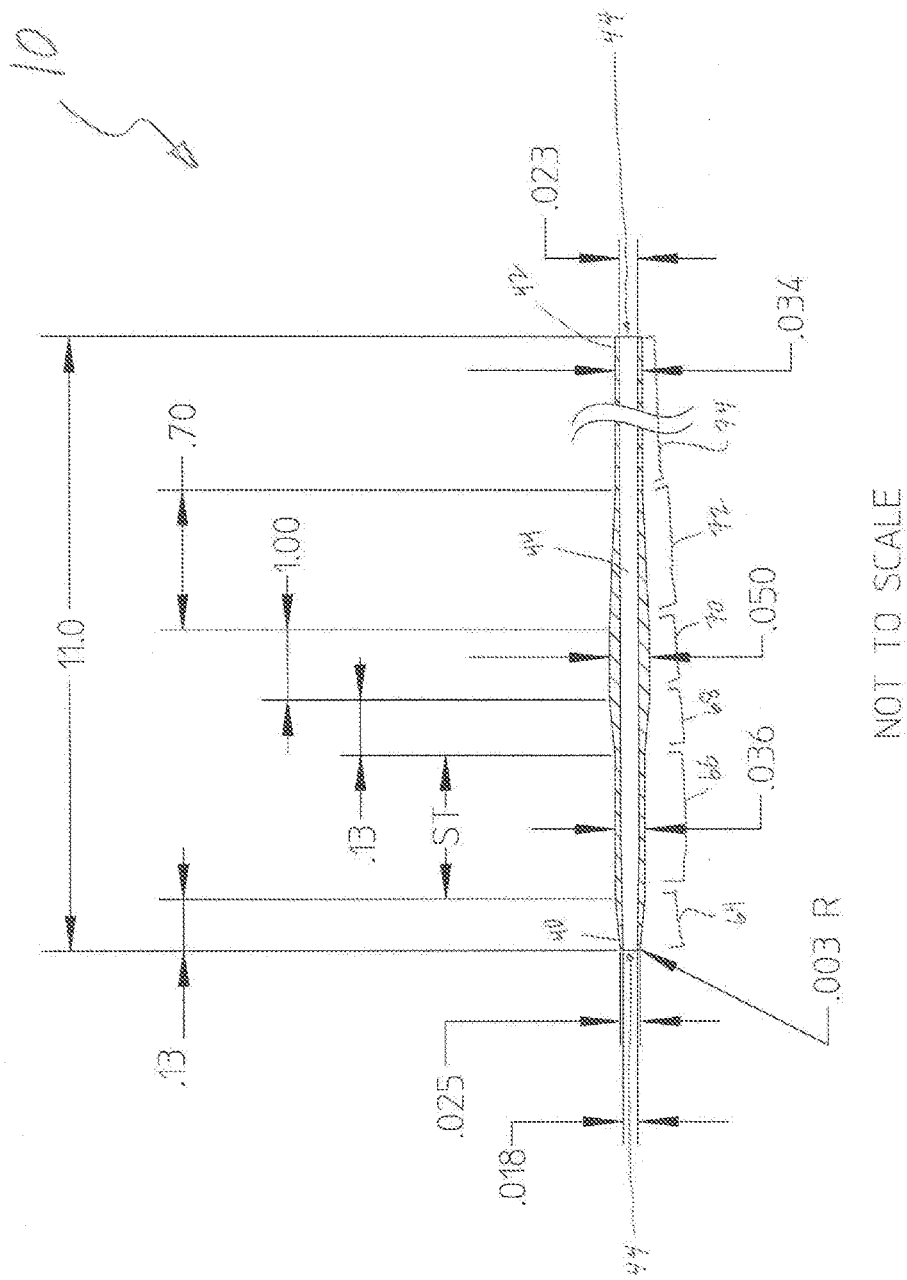
FIG. 3B illustrates a longitudinal cross sectional view of another embodiment of a dilator adaptor in accordance with the present invention.

Referring to FIG. 3B, a longitudinal cross sectional view of another embodiment of a dilator adaptor (10) is depicted with dimensions in inches. The most distal portion starting from the distal end (40) may comprise a tapered geometry (64), followed by a portion (66) having a substantially constant outer diameter for a given length, followed by another tapered portion (68), a midportion (70) which may have a mild taper either proximally or distally or be substantially constant in outer diameter for a given length, followed by a proximally tapered portion (72) which may assist with establishing a friction fit with an associated inner lumen geometry of a dilator member, as described above. A most proximal portion (74) up to the proximal end (42) may have a substantially constant outer diameter for a given length. The dilator adaptor may comprise a polymer selected from the group consisting of: polyethylene terepthalate, polyethylene, high density polyethylene, polypropylene, polytetrafluoroethylene, expanded polytetrafluoroethylene, poly (ethylene-co-vinyl acetate), poly(butyl methacrylate), and co-polymers thereof.

Figure 5:
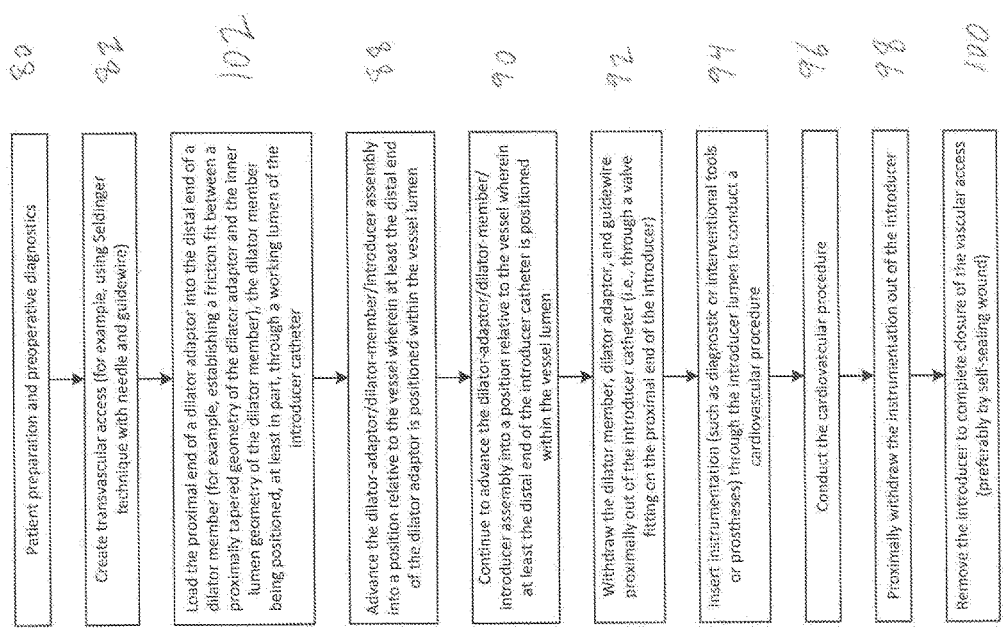
FIG. 5 illustrates a technique conducting a procedure involving a vascular access configuration in accordance with the present invention wherein a relatively small guidewire may be utilized in concert with a conventionally-sized dilator-introducer assembly.

Referring to FIG. 4, after patient preparation and preoperative diagnostics (80), access may be created (for example, by crossing with an access needle and leaving behind a guidewire, as in a Seldinger technique) (82). An operational assembly may be formed which combines the at least a portion of the guidewire through the dilator adaptor lumen, at least a portion of the dilator adaptor through the dilator member lumen, and at least a portion of the dilator member through the introducer catheter lumen. Such an assembly may be accomplished by first assembling the adaptor and dilator member together, then placing this assembly into the introducer for further advancement over the guidewire into the vessel, as shown in the embodiment of FIG. 4 (elements 84, 86); referring to FIG. 5 (102), such a sub-process may comprise combining the adaptor into an already-assembled dilator member—introducer catheter subassembly. The dilator-adaptor/dilator member/introducer assembly may then be advanced in an "over-the-wire" configuration (i.e., with the proximal end of the guidewire (and additional portions thereof following) being advanced into the distal end of the dilator-adaptor and associated dilator member and introducer as this assembly is advanced over the guidewire) into a position relative to the vessel wherein at least the distal end of the dilator adaptor is positioned within the vessel lumen (88). With the distal end of the introducer having access to the vascular lumen (90), the dilator member and dilator adaptor may be withdrawn (92) along with the guidewire, and other instrumentation may be advanced through the working lumen of the introducer catheter or sheath (94) to conduct a procedure (96), after which the instrumentation may be withdrawn out of the introducer (98), and the remaining introducer may be withdrawn to complete the closure, which preferably has been set up to be a self-sealing closure (100).

Various exemplary embodiments of the invention are described herein. Reference is made to these examples in a non-limiting sense. They are provided to illustrate more broadly applicable aspects of the invention. Various changes may be made to the invention described and equivalents may be substituted without departing from the true spirit and scope of the invention. In addition, many modifications may be made to adapt a particular situation, material, composition of matter, process, process act(s) or step(s) to the objective(s), spirit or scope of the present invention. Further, as will be appreciated by those with skill in the art that each of the individual variations described and illustrated herein has discrete components and features which may be readily separated from or combined with the features of any of the other several embodiments without departing from the scope or spirit of the present inventions. All such modifications are intended to be within the scope of claims associated with this disclosure.

Any of the devices described for carrying out the subject diagnostic or interventional procedures may be provided in packaged combination for use in executing such interventions. These supply "kits" may further include instructions for use and be packaged in sterile trays or containers as commonly employed for such purposes.

The invention includes methods that may be performed using the subject devices. The methods may comprise the act of providing such a suitable device. Such provision may be performed by the end user. In other words, the "providing" act merely requires the end user obtain, access, approach, position, set-up, activate, power-up or otherwise act to provide the requisite device in the subject method. Methods recited herein may be carried out in any order of the recited events which is logically possible, as well as in the recited order of events.

Exemplary aspects of the invention, together with details regarding material selection and manufacture have been set forth above. As for other details of the present invention, these may be appreciated in connection with the above-referenced patents and publications as well as generally known or appreciated by those with skill in the art. For example, one with skill in the art will appreciate that one or more lubricious coatings (e.g., hydrophilic polymers such as polyvinylpyrrolidone-based compositions, fluoropolymers such as tetrafluoroethylene, hydrophilic gel or silicones) may be used in connection with various portions of the devices, such as relatively large interfacial surfaces of movably coupled parts, if desired, for example, to facilitate low friction manipulation or advancement of such objects relative to other portions of the instrumentation or nearby tissue structures. The same may hold true with respect to method-based aspects of the invention in terms of additional acts as commonly or logically employed.

In addition, though the invention has been described in reference to several examples optionally incorporating various features, the invention is not to be limited to that which is described or indicated as contemplated with respect to each variation of the invention. Various changes may be made to the invention described and equivalents (whether recited herein or not included for the sake of some brevity) may be substituted without departing from the true spirit and scope of the invention. In addition, where a range of values is provided, it is understood that every intervening value, between the upper and lower limit of that range and any other stated or intervening value in that stated range, is encompassed within the invention.

Also, it is contemplated that any optional feature of the inventive variations described may be set forth and claimed independently, or in combination with any one or more of the features described herein. Reference to a singular item, includes the possibility that there are plural of the same items present. More specifically, as used herein and in claims associated hereto, the singular forms "a," "an," "said," and "the" include plural referents unless the specifically stated otherwise. In other words, use of the articles allow for "at least one" of the subject item in the description above as well as claims associated with this disclosure. It is further noted that such claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in claims associated with this disclosure shall allow for the inclusion of any additional element—irrespective of whether a given number of elements are enumerated in such claims, or the addition of a feature could be regarded as transforming the nature of an element set forth in such claims. Except as specifically defined herein, all technical and scientific terms used herein are to be given as broad a commonly understood meaning as possible while maintaining claim validity.

The breadth of the present invention is not to be limited to the examples provided and/or the subject specification, but rather only by the scope of claim language associated with this disclosure.

The invention claimed is:

1. A system for creating translumenal vascular access, comprising:
   a. a dilator-introducer assembly comprising a dilator member having proximal and distal ends and defining a dilator lumen therethrough, and an introducer member having proximal and distal ends and defining an introducer lumen therethrough, wherein the introducer lumen is defined by an inner diameter profile sized to accommodate insertion of one or more portions of the dilator member;
   b. a guidewire having an outer shape defined by a guidewire outer diameter profile;
   c. a dilator adaptor having proximal and distal ends and defining a dilator adaptor lumen therethrough, wherein the dilator adaptor lumen is defined by an inner diameter profile sized to accommodate insertion of one or more portions of the guidewire, and wherein the dilator adaptor is further defined by an outer diameter profile sized to accommodate at least partial insertion of the proximal end of the dilator adaptor into the dilator lumen, wherein the dilator adaptor, when viewed from distal end to proximal end, comprises a distal section with a substantially constant outer diameter for a distal section length, tapering up to a midsection with a substantially constant outer diameter for a midsection length, tapering down to a proximal section with a substantially constant outer diameter for a proximal section length, ending in the proximal end, wherein the substantially constant outer diameter of the proximal section is greater than that of the distal section and less than that of the midsection;
   wherein the guidewire may be advanced at least in part through the dilator adaptor lumen, the dilator adaptor may be advanced at least in part through the dilator member lumen, and the dilator member may be advanced at least in part through the introducer lumen to form an instrument assembly capable of forming substantially atraumatic outer shape profile configuration defined by longitudinally sequential increases in overall outer diameter from exposed distal ends of the guidewire, dilator adaptor, dilator member, and introducer.

2. The system of claim 1, wherein a maximum outer diameter of the guidewire is substantially smaller than a minimum inner diameter of the dilator member.

3. The system of claim 2, wherein without the dilator adaptor interposed between the guidewire and dilator member, an annular gap would be defined at the intersection of the guidewire and the distal end of the dilator member.

4. The system of claim 3, wherein the dilator adaptor inner and outer diameter profiles are configured to substantially make up the difference in fit between the guidewire and dilator member.

5. The system of claim 2, wherein the maximum outer diameter of the guidewire is at least about 25% smaller than the minimum inner diameter of the dilator member.

6. The system of claim 2, wherein the maximum outer diameter of the guidewire is about 0.018 inches.

7. The system of claim 6, wherein the minimum inner diameter of the dilator member is between about 0.035 inches and about 0.040 inches.

8. The system of claim 7, wherein the dilator adaptor has a minimum inner diameter of about 0.018 inches, and a maximum outer diameter of about 0.050 inches.

9. The system of claim 2, wherein the maximum outer diameter of the guidewire is at least about 0.01 inches smaller than the minimum inner diameter of the dilator member.

10. The system of claim 1, wherein the introducer member distal end has a tapered geometry with an outer diameter minimum at its distal tip.

11. The system of claim 1, wherein the dilator member distal end has a tapered geometry with an outer diameter minimum at its distal tip.

12. The system of claim 1, wherein the distal end of the dilator adaptor has a tapered geometry with an outer diameter minimum at its distal tip.

13. The system of claim 1, wherein at least a portion of the dilator adaptor has a proximally tapered geometry with an outer diameter minimum located adjacent its proximal end.

14. The system of claim 13, wherein a friction fit may be formed between the proximally tapered geometry of the dilator adaptor and the dilator lumen of the dilator member when loading the dilator adaptor into the dilator lumen.

15. The system of claim 14, wherein the proximally tapered geometry is selected such that one size of dilator adaptor can form a friction fit with a range of dilator lumen geometries.

16. The system of claim 1, wherein each of the distal section, midsection, and proximal sections has a substantially homogeneous inner diameter defining the dilator adaptor lumen.

17. The system of claim 1, wherein the dilator adaptor comprises a polymer selected from the group consisting of: polyethylene terepthalate, polyethylene, high density polyethylene, polypropylene, polytetrafluoroethylene, expanded polytetrafluoroethylene, poly (ethylene-co-vinyl acetate), poly(butyl methacrylate), and co-polymers thereof.

* * * * *